US012692497B2

(12) United States Patent
Schwartz et al.

(10) Patent No.: US 12,692,497 B2
(45) Date of Patent: Jul. 28, 2026

(54) CARDIAC CELL PROLIFERATION BY ADMINISTERING INHIBITORS OF SAV1, NF2, MOB1 AND/OR MUTANT SRF

(71) Applicant: Animatus Biosciences, Inc., Houston, TX (US)

(72) Inventors: Robert Joel Schwartz, Houston, TX (US); Nada Bejar, Pearland, TX (US)

(73) Assignee: Animatus Biosciences, Inc., Houston, TX (US)

( * ) Notice: Subject to any disclaimer, the term of this patent is extended or adjusted under 35 U.S.C. 154(b) by 508 days.

(21) Appl. No.: 17/969,496

(22) Filed: Oct. 19, 2022

(65) Prior Publication Data

US 2023/0193267 A1 Jun. 22, 2023

Related U.S. Application Data

(60) Provisional application No. 63/257,483, filed on Oct. 19, 2021.

(51) Int. Cl.
*C12N 15/113* (2010.01)
*C12N 5/077* (2010.01)
*C12N 15/88* (2006.01)

(52) U.S. Cl.
CPC .......... *C12N 15/113* (2013.01); *C12N 5/0657* (2013.01); *C12N 15/88* (2013.01); *C12N 2310/14* (2013.01)

(58) Field of Classification Search
CPC .... C12N 15/113; C12N 5/0657; C12N 15/88; C12N 2310/14; C12N 2320/31; A61K 31/713
See application file for complete search history.

(56) References Cited

U.S. PATENT DOCUMENTS

2006/0172374 A1* 8/2006 Bichsel ........................ 435/69.1
2016/0312219 A1* 10/2016 Martin ................. C12N 15/113
2020/0016212 A1* 1/2020 Monroe ................. A61K 35/34

FOREIGN PATENT DOCUMENTS

WO WO2003035845 A2 * 5/2003
WO WO2017189730 * 11/2017
WO WO2019136031 A1 * 7/2019 ......... A61K 38/1709

OTHER PUBLICATIONS

Asian journal of pharmaceutical sciences vol. 14,5 (2019): 497-510. doi:10.1016/j.ajps.2018.12.005 (Year: 2019).*

* cited by examiner

Primary Examiner — Tracy Vivlemore
(74) Attorney, Agent, or Firm — Eric P. Mirabel, JD, LLM

(57) ABSTRACT

Disclosed are DsiRNA inhibitors for the genes encoding SAV1, NF2 and MOB1, which cause proliferation of cardiomyocytes on administration to a mammal. The DsiRNA inhibitors can also be administered with a mutant SRF (153-A3) or an mRNA encoding it, and/or Yap5SA (a Yap mutant) or an encoding mRNA, which enhance the proliferative effect on cardiomyocytes. Mutant SRF (153-A3) with Yap5SA alone also induce myocyte replication.

6 Claims, 13 Drawing Sheets
(9 of 13 Drawing Sheet(s) Filed in Color)
Specification includes a Sequence Listing.

A.

B.

UNIVERSITY of HOUSTON RESEARCH
Office of Technology Transfer and Innovation
fig. 6
A.
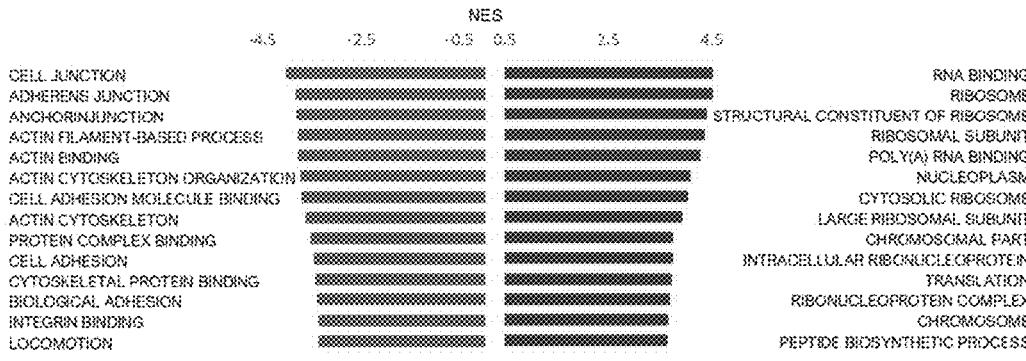
B.
C.
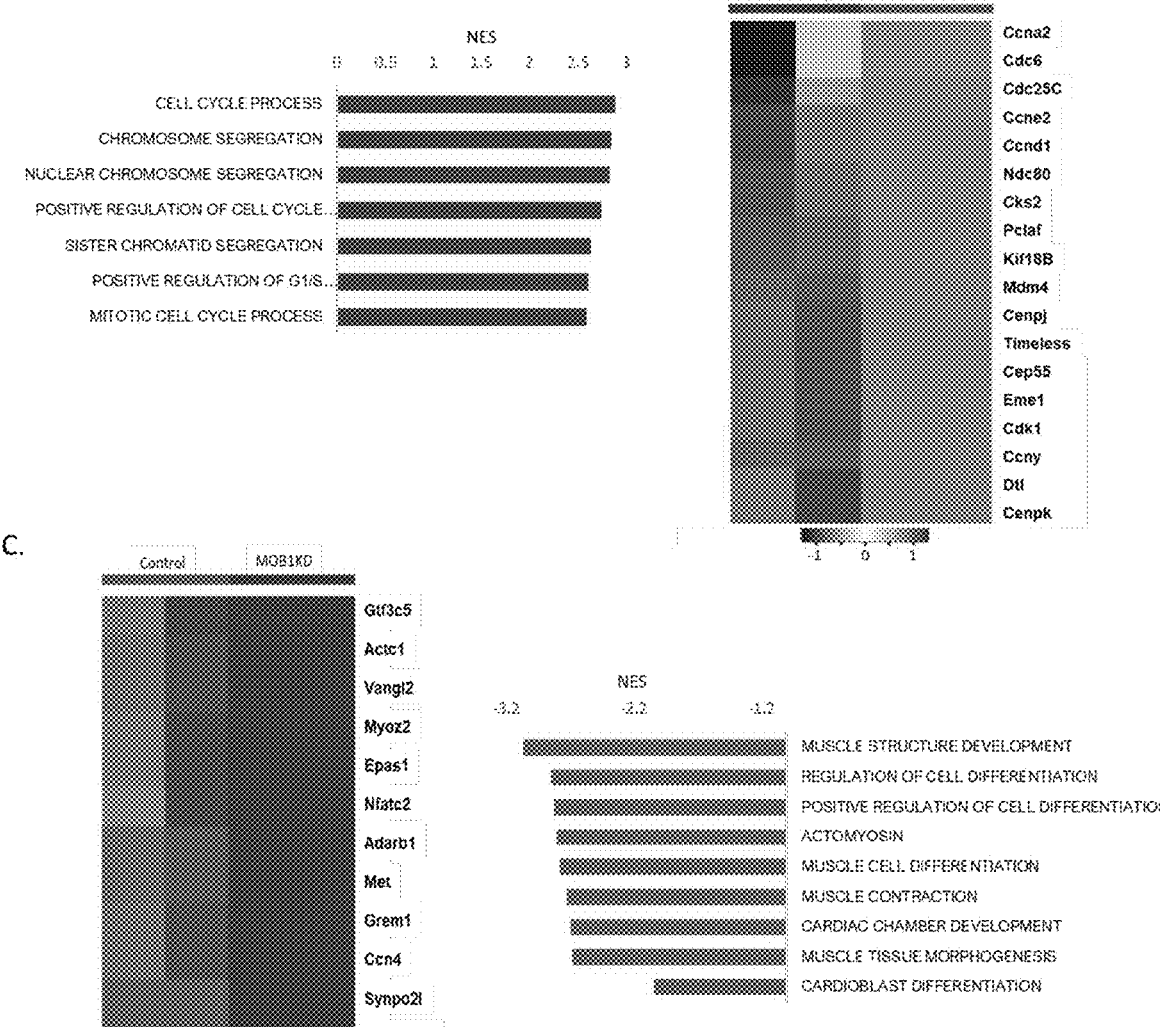

Fig.  8A                Fig.       8B
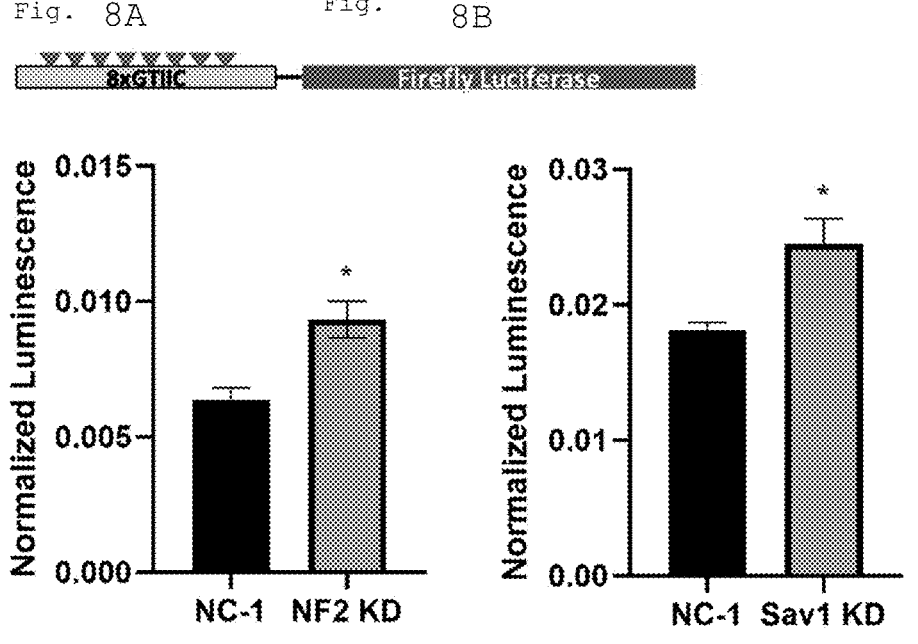
fig9A                          fig 9B
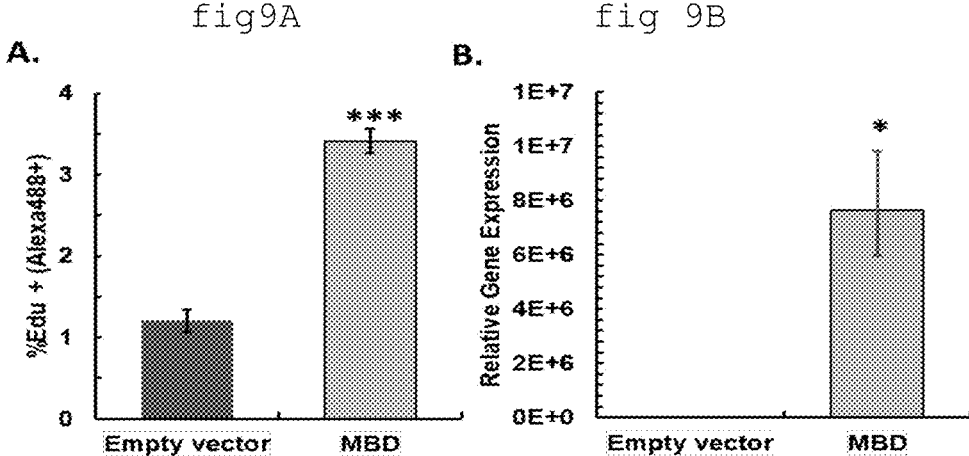

SEQUENCE LISTING

```
Sequence total quantity: 76
SEQ ID NO: 1               moltype = RNA   length = 25
FEATURE                    Location/Qualifiers
source                     1..25
                           mol_type = other RNA
                           organism = synthetic construct
SEQUENCE: 1
ggcaacttac tatttggaat tacaa                                        25

SEQ ID NO: 2               moltype = RNA   length = 27
FEATURE                    Location/Qualifiers
source                     1..27
                           mol_type = other RNA
                           organism = synthetic construct
```

```
SEQUENCE: 2
ttccgttgaa tgataaacct taatgtt                                          27

SEQ ID NO: 3              moltype = RNA   length = 25
FEATURE                   Location/Qualifiers
source                    1..25
                          mol_type = other RNA
                          organism = synthetic construct
modified_base             24
                          mod_base = OTHER
                          note = THYMINE
SEQUENCE: 3
atattatgaa tacaaccatg atctc                                            25

SEQ ID NO: 4              moltype = RNA   length = 27
FEATURE                   Location/Qualifiers
source                    1..27
                          mol_type = other RNA
                          organism = synthetic construct
SEQUENCE: 4
tctataatac ttatgttggt actagag                                         27

SEQ ID NO: 5              moltype = RNA   length = 25
FEATURE                   Location/Qualifiers
source                    1..25
                          mol_type = other RNA
                          organism = synthetic construct
SEQUENCE: 5
ggaatctcat gccttcattc attcg                                           25

SEQ ID NO: 6              moltype = RNA   length = 27
FEATURE                   Location/Qualifiers
source                    1..27
                          mol_type = other RNA
                          organism = synthetic construct
SEQUENCE: 6
cgccttagag tacggaagta agtaagc                                         27

SEQ ID NO: 7              moltype = RNA   length = 25
FEATURE                   Location/Qualifiers
source                    1..25
                          mol_type = other RNA
                          organism = synthetic construct
modified_base             24
                          mod_base = OTHER
                          note = THYMINE
SEQUENCE: 7
cgaggtgtct aagccggccg aggtg                                           25

SEQ ID NO: 8              moltype = RNA   length = 27
FEATURE                   Location/Qualifiers
source                    1..27
                          mol_type = other RNA
                          organism = synthetic construct
SEQUENCE: 8
ttgctccaca gattcggccg gctccac                                         27

SEQ ID NO: 9              moltype = RNA   length = 25
FEATURE                   Location/Qualifiers
source                    1..25
                          mol_type = other RNA
                          organism = synthetic construct
SEQUENCE: 9
cgtcgttgag ccggctgact tcccg                                           25

SEQ ID NO: 10             moltype = RNA   length = 27
FEATURE                   Location/Qualifiers
source                    1..27
                          mol_type = other RNA
                          organism = synthetic construct
SEQUENCE: 10
ccgcagcaac tcggccgact gaagggc                                         27

SEQ ID NO: 11             moltype = RNA   length = 25
FEATURE                   Location/Qualifiers
source                    1..25
                          mol_type = other RNA
                          organism = synthetic construct
modified_base             25
```

```
                              mod_base = OTHER
                              note = THYMINE
SEQUENCE: 11
gatttggaac cttattgtga taaat                                                25

SEQ ID NO: 12           moltype = RNA   length = 27
FEATURE                 Location/Qualifiers
source                  1..27
                        mol_type = other RNA
                        organism = synthetic construct
SEQUENCE: 12
tcctaaacct tggaataaca ctattta                                              27

SEQ ID NO: 13           moltype = RNA   length = 25
FEATURE                 Location/Qualifiers
source                  1..25
                        mol_type = other RNA
                        organism = synthetic construct
SEQUENCE: 13
actgaaagaa atcagtccct tctgg                                                25

SEQ ID NO: 14           moltype = RNA   length = 27
FEATURE                 Location/Qualifiers
source                  1..27
                        mol_type = other RNA
                        organism = synthetic construct
SEQUENCE: 14
tttgactttc tttagtcagg gaagacc                                              27

SEQ ID NO: 15           moltype = RNA   length = 25
FEATURE                 Location/Qualifiers
source                  1..25
                        mol_type = other RNA
                        organism = synthetic construct
modified_base           24
                        mod_base = OTHER
                        note = THYMINE
SEQUENCE: 15
caattccaag acgaactgat atctg                                                25

SEQ ID NO: 16           moltype = RNA   length = 27
FEATURE                 Location/Qualifiers
source                  1..27
                        mol_type = other RNA
                        organism = synthetic construct
SEQUENCE: 16
ttgttaaggt tctgcttgac tatagac                                              27

SEQ ID NO: 17           moltype = RNA   length = 25
FEATURE                 Location/Qualifiers
source                  1..25
                        mol_type = other RNA
                        organism = synthetic construct
modified_base           24
                        mod_base = OTHER
                        note = THYMINE
SEQUENCE: 17
cagtaaggac ctgactagaa gcatg                                                25

SEQ ID NO: 18           moltype = RNA   length = 27
FEATURE                 Location/Qualifiers
source                  1..27
                        mol_type = other RNA
                        organism = synthetic construct
SEQUENCE: 18
gtgtcattcc tggactgatc ttcgtac                                              27

SEQ ID NO: 19           moltype = RNA   length = 25
FEATURE                 Location/Qualifiers
source                  1..25
                        mol_type = other RNA
                        organism = synthetic construct
SEQUENCE: 19
ccttggtact gaaacagtaa gtcac                                                25

SEQ ID NO: 20           moltype = RNA   length = 28
FEATURE                 Location/Qualifiers
source                  1..28
                        mol_type = other RNA
```

-continued

```
                         organism = synthetic construct
SEQUENCE: 20
atggaaccat gactttgtac attcagtg                                       28

SEQ ID NO: 21            moltype = RNA   length = 25
FEATURE                  Location/Qualifiers
source                   1..25
                         mol_type = other RNA
                         organism = synthetic construct
SEQUENCE: 21
gctagaaagc agatggaaag gcagc                                          25

SEQ ID NO: 22            moltype = RNA   length = 27
FEATURE                  Location/Qualifiers
source                   1..27
                         mol_type = other RNA
                         organism = synthetic construct
SEQUENCE: 22
tccgatcttt cgtctacctt tccgtcg                                        27

SEQ ID NO: 23            moltype = RNA   length = 25
FEATURE                  Location/Qualifiers
source                   1..25
                         mol_type = other RNA
                         organism = synthetic construct
SEQUENCE: 23
ggaggagcta gttcaagaga tcacg                                          25

SEQ ID NO: 24            moltype = RNA   length = 27
FEATURE                  Location/Qualifiers
source                   1..27
                         mol_type = other RNA
                         organism = synthetic construct
SEQUENCE: 24
ctcctcctcg atcaagttct ctagtgc                                        27

SEQ ID NO: 25            moltype = RNA   length = 25
FEATURE                  Location/Qualifiers
source                   1..25
                         mol_type = other RNA
                         organism = synthetic construct
modified_base            24
                         mod_base = OTHER
                         note = THYMINE
SEQUENCE: 25
ggctgatcag ttaaagcaag acttg                                          25

SEQ ID NO: 26            moltype = RNA   length = 27
FEATURE                  Location/Qualifiers
source                   1..27
                         mol_type = other RNA
                         organism = synthetic construct
SEQUENCE: 26
ctccgactag tcaatttcgt tctgaac                                        27

SEQ ID NO: 27            moltype = RNA   length = 25
FEATURE                  Location/Qualifiers
source                   1..25
                         mol_type = other RNA
                         organism = synthetic construct
SEQUENCE: 27
atgagcttca gctctctcaa gagga                                          25

SEQ ID NO: 28            moltype = RNA   length = 30
FEATURE                  Location/Qualifiers
source                   1..30
                         mol_type = other RNA
                         organism = synthetic construct
SEQUENCE: 28
cgtactcgaa gtcgagagag ttcttctcct                                     30

SEQ ID NO: 29            moltype = RNA   length = 25
FEATURE                  Location/Qualifiers
source                   1..25
                         mol_type = other RNA
                         organism = synthetic construct
modified_base            24
                         mod_base = OTHER
                         note = THYMINE
```

```
SEQUENCE: 29
gacataccaa gcttcaacct cattg                                         25

SEQ ID NO: 30          moltype = RNA   length = 27
FEATURE                Location/Qualifiers
source                 1..27
                       mol_type = other RNA
                       organism = synthetic construct
SEQUENCE: 30
gactgtatgg ttcgaagttg gagtaac                                       27

SEQ ID NO: 31          moltype = RNA   length = 25
FEATURE                Location/Qualifiers
source                 1..25
                       mol_type = other RNA
                       organism = synthetic construct
SEQUENCE: 31
gaattactgc ttggtacgca gagca                                         25

SEQ ID NO: 32          moltype = RNA   length = 27
FEATURE                Location/Qualifiers
source                 1..27
                       mol_type = other RNA
                       organism = synthetic construct
SEQUENCE: 32
ctcttaatga cgaaccatgc gtctcgt                                       27

SEQ ID NO: 33          moltype = RNA   length = 25
FEATURE                Location/Qualifiers
source                 1..25
                       mol_type = other RNA
                       organism = synthetic construct
modified_base          24
                       mod_base = OTHER
                       note = THYMINE
SEQUENCE: 33
cttcaggaac taattgagaa gcttg                                         25

SEQ ID NO: 34          moltype = RNA   length = 27
FEATURE                Location/Qualifiers
source                 1..27
                       mol_type = other RNA
                       organism = synthetic construct
SEQUENCE: 34
gtgaagtcct tgattaactc ttcgaac                                       27

SEQ ID NO: 35          moltype = RNA   length = 25
FEATURE                Location/Qualifiers
source                 1..25
                       mol_type = other RNA
                       organism = synthetic construct
SEQUENCE: 35
actgaagcaa ctgcattgaa attca                                         25

SEQ ID NO: 36          moltype = RNA   length = 27
FEATURE                Location/Qualifiers
source                 1..27
                       mol_type = other RNA
                       organism = synthetic construct
SEQUENCE: 36
aatgacttcg ttgacgtaac tttaagt                                       27

SEQ ID NO: 37          moltype = RNA   length = 25
FEATURE                Location/Qualifiers
source                 1..25
                       mol_type = other RNA
                       organism = synthetic construct
SEQUENCE: 37
ggacctcaat gaatggattg ctgtt                                         25

SEQ ID NO: 38          moltype = RNA   length = 25
FEATURE                Location/Qualifiers
source                 1..25
                       mol_type = other RNA
                       organism = synthetic construct
SEQUENCE: 38
cctggagtta cttacctaac gacaa                                         25

SEQ ID NO: 39          moltype = RNA   length = 25
```

-continued

```
FEATURE              Location/Qualifiers
source               1..25
                     mol_type = other RNA
                     organism = synthetic construct
SEQUENCE: 39
ggatctaaag acagataaat gtttc                                            25

SEQ ID NO: 40        moltype = RNA   length = 25
FEATURE              Location/Qualifiers
source               1..25
                     mol_type = other RNA
                     organism = synthetic construct
SEQUENCE: 40
cctagatttc tgtctattta caaag                                           25

SEQ ID NO: 41        moltype = RNA   length = 25
FEATURE              Location/Qualifiers
source               1..25
                     mol_type = other RNA
                     organism = synthetic construct
SEQUENCE: 41
ggtatggact aaatgatact gacta                                           25

SEQ ID NO: 42        moltype = RNA   length = 25
FEATURE              Location/Qualifiers
source               1..25
                     mol_type = other RNA
                     organism = synthetic construct
SEQUENCE: 42
ccatacctga tttactatga ctgat                                           25

SEQ ID NO: 43        moltype = RNA   length = 25
FEATURE              Location/Qualifiers
source               1..25
                     mol_type = other RNA
                     organism = synthetic construct
modified_base        25
                     mod_base = OTHER
                     note = THYMINE
SEQUENCE: 43
gcaggtccga gatatgaata tcact                                           25

SEQ ID NO: 44        moltype = RNA   length = 27
FEATURE              Location/Qualifiers
source               1..27
                     mol_type = other RNA
                     organism = synthetic construct
SEQUENCE: 44
gacgtccagg ctctatactt atagtga                                         27

SEQ ID NO: 45        moltype = RNA   length = 25
FEATURE              Location/Qualifiers
source               1..25
                     mol_type = other RNA
                     organism = synthetic construct
modified_base        24
                     mod_base = OTHER
                     note = THYMINE
SEQUENCE: 45
gtgatagttt ccgagtaaga cctta                                           25

SEQ ID NO: 46        moltype = RNA   length = 27
FEATURE              Location/Qualifiers
source               1..27
                     mol_type = other RNA
                     organism = synthetic construct
SEQUENCE: 46
cacactatca aaggctcatt ctggaat                                         27

SEQ ID NO: 47        moltype = RNA   length = 25
FEATURE              Location/Qualifiers
source               1..25
                     mol_type = other RNA
                     organism = synthetic construct
modified_base        24..25
                     mod_base = OTHER
                     note = THYMINE
SEQUENCE: 47
caaagactat tctaaagcgt ctgtt                                           25
```

-continued

```
SEQ ID NO: 48          moltype = RNA  length = 27
FEATURE                Location/Qualifiers
source                 1..27
                       mol_type = other RNA
                       organism = synthetic construct
SEQUENCE: 48
ccgtttctga taagatttcg cagacaa                                        27

SEQ ID NO: 49          moltype = AA  length = 20
FEATURE                Location/Qualifiers
source                 1..20
                       mol_type = protein
                       organism = synthetic construct
SEQUENCE: 49
PGKKTRGRVK IKMEFIDNKL                                                20

SEQ ID NO: 50          moltype = AA  length = 20
FEATURE                Location/Qualifiers
source                 1..20
                       mol_type = protein
                       organism = synthetic construct
SEQUENCE: 50
PGKKTRGRVK IKMEFIDAAA                                                20

SEQ ID NO: 51          moltype = AA  length = 20
FEATURE                Location/Qualifiers
source                 1..20
                       mol_type = protein
                       organism = synthetic construct
SEQUENCE: 51
PGKKTAAAVK IKMEFIDNKL                                                20

SEQ ID NO: 52          moltype = AA  length = 20
FEATURE                Location/Qualifiers
source                 1..20
                       mol_type = protein
                       organism = synthetic construct
SEQUENCE: 52
PGKKTRGRAA AKMEFIDNKL                                                20

SEQ ID NO: 53          moltype = AA  length = 20
FEATURE                Location/Qualifiers
source                 1..20
                       mol_type = protein
                       organism = synthetic construct
SEQUENCE: 53
PGKKTRGRVK IAAAFIDNKL                                                20

SEQ ID NO: 54          moltype = AA  length = 20
FEATURE                Location/Qualifiers
source                 1..20
                       mol_type = protein
                       organism = synthetic construct
SEQUENCE: 54
PGKKTRGRVK IKMEAAANKL                                                20

SEQ ID NO: 55          moltype = AA  length = 20
FEATURE                Location/Qualifiers
source                 1..20
                       mol_type = protein
                       organism = synthetic construct
SEQUENCE: 55
PGKKTRGRVK IKMEFIDNAL                                                20

SEQ ID NO: 56          moltype = AA  length = 20
FEATURE                Location/Qualifiers
source                 1..20
                       mol_type = protein
                       organism = synthetic construct
SEQUENCE: 56
PGKKTRGRVK IKMEFIDNKA                                                20

SEQ ID NO: 57          moltype = AA  length = 48
FEATURE                Location/Qualifiers
source                 1..48
                       mol_type = protein
                       organism = synthetic construct
SEQUENCE: 57
```

-continued

```
SGAKPGKKTR GRVKIKMEFI DNKLRRYTTF SKRKTGIMKK AYELSTLT                    48

SEQ ID NO: 58          moltype = AA   length = 7
FEATURE                Location/Qualifiers
source                 1..7
                       mol_type = protein
                       organism = synthetic construct
SEQUENCE: 58
KMEFIDN                                                                  7

SEQ ID NO: 59          moltype = DNA  length = 21
FEATURE                Location/Qualifiers
source                 1..21
                       mol_type = other DNA
                       organism = synthetic construct
SEQUENCE: 59
ctgtcccgca agaaaaccaa a                                                  21

SEQ ID NO: 60          moltype = DNA  length = 21
FEATURE                Location/Qualifiers
source                 1..21
                       mol_type = other DNA
                       organism = synthetic construct
SEQUENCE: 60
aatgaaggca tgagattccg c                                                  21

SEQ ID NO: 61          moltype = DNA  length = 19
FEATURE                Location/Qualifiers
source                 1..19
                       mol_type = other DNA
                       organism = synthetic construct
SEQUENCE: 61
gccatcgctt ctcgcatga                                                     19

SEQ ID NO: 62          moltype = DNA  length = 21
FEATURE                Location/Qualifiers
source                 1..21
                       mol_type = other DNA
                       organism = synthetic construct
SEQUENCE: 62
cgcagttgaa ctccatctcg g                                                  21

SEQ ID NO: 63          moltype = DNA  length = 21
FEATURE                Location/Qualifiers
source                 1..21
                       mol_type = other DNA
                       organism = synthetic construct
SEQUENCE: 63
ggcaggtccc aggtatgaat a                                                  21

SEQ ID NO: 64          moltype = DNA  length = 21
FEATURE                Location/Qualifiers
source                 1..21
                       mol_type = other DNA
                       organism = synthetic construct
SEQUENCE: 64
tcaagctgat cctgaaccca a                                                  21

SEQ ID NO: 65          moltype = DNA  length = 19
FEATURE                Location/Qualifiers
source                 1..19
                       mol_type = other DNA
                       organism = synthetic construct
SEQUENCE: 65
caaggaccgc acagcagtt                                                     19

SEQ ID NO: 66          moltype = DNA  length = 20
FEATURE                Location/Qualifiers
source                 1..20
                       mol_type = other DNA
                       organism = synthetic construct
SEQUENCE: 66
agaacaggcg ctccactctg                                                    20

SEQ ID NO: 67          moltype = DNA  length = 21
FEATURE                Location/Qualifiers
source                 1..21
                       mol_type = other DNA
                       organism = synthetic construct
```

-continued

```
SEQUENCE: 67
aggtcggtgt gaacggattt g                                             21

SEQ ID NO: 68          moltype = DNA  length = 23
FEATURE                Location/Qualifiers
source                 1..23
                       mol_type = other DNA
                       organism = synthetic construct
SEQUENCE: 68
tgtagaccat gtagttgagg tca                                           23

SEQ ID NO: 69          moltype = DNA  length = 20
FEATURE                Location/Qualifiers
source                 1..20
                       mol_type = other DNA
                       organism = synthetic construct
SEQUENCE: 69
atgagcagcg gactgccacg                                               20

SEQ ID NO: 70          moltype = DNA  length = 20
FEATURE                Location/Qualifiers
source                 1..20
                       mol_type = other DNA
                       organism = synthetic construct
SEQUENCE: 70
gtccagggtg ccgcacatgg                                               20

SEQ ID NO: 71          moltype = DNA  length = 23
FEATURE                Location/Qualifiers
source                 1..23
                       mol_type = other DNA
                       organism = synthetic construct
SEQUENCE: 71
cccggagcca gaaaaccact ggt                                           23

SEQ ID NO: 72          moltype = DNA  length = 21
FEATURE                Location/Qualifiers
source                 1..21
                       mol_type = other DNA
                       organism = synthetic construct
SEQUENCE: 72
gtccacaagg atggcccgca t                                             21

SEQ ID NO: 73          moltype = DNA  length = 22
FEATURE                Location/Qualifiers
source                 1..22
                       mol_type = other DNA
                       organism = synthetic construct
SEQUENCE: 73
ggctgggttc ccctgcagac at                                            22

SEQ ID NO: 74          moltype = DNA  length = 22
FEATURE                Location/Qualifiers
source                 1..22
                       mol_type = other DNA
                       organism = synthetic construct
SEQUENCE: 74
tgggcaaagc catggcctga ga                                            22

SEQ ID NO: 75          moltype = DNA  length = 21
FEATURE                Location/Qualifiers
source                 1..21
                       mol_type = other DNA
                       organism = synthetic construct
SEQUENCE: 75
tttcggcctt gccagagcgt t                                             21

SEQ ID NO: 76          moltype = DNA  length = 20
FEATURE                Location/Qualifiers
source                 1..20
                       mol_type = other DNA
                       organism = synthetic construct
SEQUENCE: 76
gtggagtagc gagccgagcc                                               20
```

CARDIAC CELL PROLIFERATION BY ADMINISTERING INHIBITORS OF SAV1, NF2, MOB1 AND/OR MUTANT SRF

SEQUENCE LISTING

The instant application contains a Sequence Listing which has been submitted electronically in xml format and is hereby incorporated by reference in its entirety. Said xml copy, created on Jan. 1, 2023, is named 202223_5086.xml and is 72,000 bytes in size.

BACKGROUND

Methods of promoting replication of cardiac cells for the purpose of, for example, improving heart health and athletic performance, can be effected by manipulation of the Hippo pathway. The Hippo pathway is a cell signaling pathway involved in cellular proliferation, stem cell differentiation, control of organ size and apoptosis. The pathway's main effector is a transcriptional co-factor YAP (Yes-associated protein) whose activation is controlled by different regulators like SAV1 (Salvador Homolog 1), NF2 (Neurofibromin 2) and MOB1 (Mps one binder kinase activator). To date, no one has disclosed how to effectively manipulate any of these factors to promote replication of cardiac cells.

SUMMARY

The invention relates to dicer substrate siRNAs (DsiR-NAs) for administration to a mammal, as inhibitors of one or more of the following: (1) For Salvador Homolog 1 (SAV1) inhibition, one would use one or more of the eight complementary polynucleotide pairs in SEQ ID NOS: 1-16, and for inhibition of human SAV1, one would use one or more of the three complementary polynucleotide pairs in SEQ ID NOS: 11-16; (2) For Neurofibromin 2 (NF2) protein inhibition, one would use one or more of the eight complementary polynucleotide pairs in SEQ ID NOS: 17-32, and for inhibition of human NF2, one would use one or more of the three complementary polynucleotide pairs in SEQ ID NOS: 27-32; (3) For Mps one binder kinase activator (MOB1) protein inhibition, one would use one or more of the eight complementary polynucleotide pairs in SEQ ID NOS: 33-48), and for inhibition of human MOB1, one would use one or more of the three complementary polynucleotide pairs in SEQ ID NOS: 43-48.

Such a DsiRNA composition can also include a mutant serum response factor (SRF) or mRNA encoding it, wherein the wild type has the following protein sequence: PGKKTR-GRVKIKMEFIDNKL (SEQ ID NO: 49), and the mutant SRFs include Stemin (also designated SRF 153 (A3) based on alanine mutation locations), where Stemin has the protein sequence PGKKTRGRVKIKMEFIDAAA (SEQ ID NO: 50)) or one of the other mutant SRFs in

TABLE I

| Table I, Alanine Scanning Mutations of SRF |
| --- |
| 141(A3) PGKKTAAAVKIKMEFIDNKL (SEQ ID NO: 51) |
| 144(A3) PGKKTRGRAAAKMEFIDNKL (SEQ ID NO: 52) |
| 147(A3) PGKKTRGRVKIAAAFIDNKL (SEQ ID NO: 53) |
| 150(A3) an PGKKTRGRVKIKMEAAANKL (SEQ ID NO: 54) |

TABLE I-continued

| Table I, Alanine Scanning Mutations of SRF |
| --- |
| 154(A) PGKKTRGRVKIKMEFIDNAL (SEQ ID NO: 55) |
| 155(A) PGKKTRGRVKIKMEFIDNKA (SEQ ID NO: 56) |

The compositions of the invention include one or more of the aforementioned DsiRNA inhibitors, or analogs with at least 95% sequence identity to the aforementioned DsiRNA inhibitors, and can also include Stemin (153 (A3)) or one or more of the other mutant SRFs or mRNAs encoding Stemin or such other mutant SRFs.

The compositions of the invention are useful for inducing cardiac cell proliferation (such cells including cardiomyocytes) in vitro or vivo in mammals, which is useful for making a mammal heart healthier and stronger, which would be useful for increased health and vitality in mammals, and would be particularly useful for mammals engaging in high activity levels or requiring endurance, such race horses, equestrian event horses, bucking livestock, and hunting and herding dogs. Such compositions be administered to a mammal in a pharmaceutical formulation to induce proliferation of the cardiac cells.

The mutant SRF can include at least 20 residues of the sequence SGAKPGKKTRGRVKIKMEFIDNKLR-RYTTFSKRKTGIMKKAYELSTLT (SEQ ID NO: 57) or the mRNA encoding it. In some embodiments, the mutant SRF includes a mutation or mutations selected from an insertion, deletions or substitution in region of KMEFIDN (SEQ ID NO: 58). The mutant SRF can also include any one of the sequences in SEQ ID NOS: 50-56 or the encoding mRNAs. In some embodiments, the mutant SRF includes any one of the mutant SRFs listed in US Publ'n No. 2021/0069294 or U.S. Pat. No. 11,179,479B1 (both are incorporated by reference) and the mRNAs encoding these mutant SRFs.

The mutant SRFs may be in the form of a polypeptide or a protein, or a nucleotide sequence (DNA or mRNA) that expresses the mutant SRF, or combinations thereof.

A composition with mutant SRF153 (A3) with Yap5SA alone also induces myocyte replication.

Composition Components

The compositions of the invention suitable for administration to a mammal can include various excipients including, anti-adherents, binders, coatings, colors, disintegrants, flavors, glidants, lubricants, preservatives, sorbents, sweeteners, vehicles, or combinations thereof.

In some embodiments, the compositions may also include a delivery vehicle, and a delivery vehicle including particles. Such particles include nanoparticles, liposomes, or combinations thereof, and particles wherein the one or more inhibitors are encapsulated in the particles.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A are Western blots showing post-transfection knockdown ("KD") of each protein. In FIGS. 1A, 1B, the data is a representation of one experiment done 3 times, where "*" indicates a statistically significant difference between the control and the treatment, P<0.01. FIG. 1B shows post-transfection knockdown of each protein transcript; FIG. 1C shows transcript level of CTGF, AuroraKB and CDC2 following SAV1 KD, NF2 KD or MOB1 KD.

FIG. 2A shows MOB1 knockdown post-transfection, as determined by Edu incorporation. In FIG. 2B it shows the effect on the myocytes of MOB1 knockdown as measured by EdU immunofluorescence at 48 h post MOB1 DsiRNA transfection.

FIG. 3 upper panel, shows cell confluence at the time of the transfection (0 h) or 48 h after transfection (48 h) with an applied confluence mask. Scale represents 200 microns. FIG. 3 lower panel, shows the percentage of the confluency of the cells over time, and that there is an increase in MOB1 KD cell confluency. Data is the mean of 2 independent experiments. Error bars represent the standard error.

FIGS. 4A & 4B show EdU proliferation imaging results, where the scale bars in FIG. 4B represent 100 microns, imaging analysis representing the mean of 4 independent experiments, and "*" indicates a significant difference between the indicated treatment ("*" indicates P<0.05; "*" indicates P<0.01; "**" indicates P<0.001). Error bars represent the SEM;

FIG. 4B are Western blots showing a decrease of both NF2 and SAV1 levels in double-knockdown (NF2 and SAV1) DsiRNA treated cells. FIG. 4C shows the effects of DsiRNA knockdnown, and combinations of DsiRNA knockdnowns, of other proteins, on determined by an EdU proliferation assay.

FIGS. 6A, 6B & 6C show the results of a differential gene expression analysis, following treating Rat neonatal cardiomyocytes with 10 pmols of equal proportions of the DsiRNA pairs for MOB1: SEQ ID NO: 33; SEQ ID NO: 34 and SEQ ID NO: 35; SEQ ID NO: 36, 48 h post DsiRNA transfection. The results are a representation of relevant pathways for cell proliferation and cardiac dedifferentiation. Normalized enrichment score (NES) is represented. FIG. 6A, left side, shows top 15 downregulated pathways and the right side shows the top 15 upregulated pathways. FIG. 6B shows cell cycle pathways upregulated after MOB1 knockdown and heatmap representation of relevant genes. FIG. 6C shows the heatmap of relevant gene expression related to muscle and heart differentiation and contraction and down-regulated pathways.

FIGS. 7A, 7C, 7D, 7F, 7G to 7I show relative gene expression profiles for transcripts encoding SAV1, NF2, and MOB1, and FIGS. 7B, 7E, and 7H show Edu assay results for SAV1, NF2, and MOB1, where NIH3t3 mouse fibroblast cells were transfected with equal proportions of the following SAV1 KD, NF2 KD, and MOB1 KD DsiRNAs pairs, i.e., for SAV1 KD: SEQ ID NO: 5; SEQ ID NO: 6 (dsiRNA #1) with SEQ ID NO: 7; SEQ ID NO: 8 (dsiRNA #2) with SEQ ID NO: 9; SEQ ID NO: 10 (dsiRNA #3)); for NF2 KD: SEQ ID NO: 21; SEQ ID NO: 22 (dsiRNA #1) with SEQ ID NO: 23; SEQ ID NO: 24 (dsiRNA #2) with SEQ ID NO: 25; SEQ ID NO: 26 (dsiRNA #3); and for MOB-1 KD: SEQ ID NO: 37; SEQ ID NO: 38 (dsiRNA #1) with SEQ ID NO: 39; SEQ ID NO: 40 (dsiRNA #2) and SEQ ID NO: 41; with SEQ ID NO: 42 (dsiRNA #2), where gene silencing was verified with RT-PCR. NC-1 dsiRNA is a non-targeting siRNA. All three tested gene DsiRNAs were effective in reducing SAV1, NF2 and MOB1 transcript levels. FIG. 7A shows transcript level of SAV1 72 h post transfection; FIG. 7B shows EdU incorporation level in a flow cytometry assay 72 h post SAV1 transfection; FIG. 7C shows CTGF transcript level 72 h post SAV1 KD; FIG. 7D shows transcript levels of NF2 72 h post transfection; FIG. 7E shows EdU incorporation level on a flow cytometry assay 72 h post NF2 transfection; FIG. 7D shows CTGF transcript level 72 h post NF2 K; FIG. 7G shows) transcript level of MOB1 72 h post transfection; FIG. 7H shows EdU incorporation level in a flow cytometry assay 72 h post MOB1 DsiRNAs transfection; and FIG. 7I shows CTGF transcript level 72 h post MOB1 KD.

FIGS. 8A, 8B show the results of a luciferase assay on NIH3t3 cells (a fibroblast cell line that was isolated from a mouse NIH/Swiss embryo), 24 h post NF2 DsiRNA transfection (FIG. 8A) and 24 h post SAV1 DsiRNA transfection (FIG. 8B), where the NC-1 gene expression is a control.

FIGS. 9A, 9B show the results of a assay demonstrating the effect of overexpression of MOB Binding Domain (MBD) peptide on NIH3t3 fibroblasts, 96 h post plating. FIG. 9A is a flow cytometry EdU assay demonstrating that MBD overexpression induces cell proliferation 96 h post treatment. FIG. 9B shows relative gene expression in the NIH3t3 fibroblasts. "***" indicates P<0.001.

FIG. 12A is a schematic diagram of the SRF regulatory domains including the MADS box. Cofactors Nkx2-5, Gata4/6, Crp2, and inhibitor Hop1 bind to the N-terminal extension. ETS factors Elkland SAP1 bind to the beta loop and compete with MRTF-A. Tead factors bind to the 2^nd^ alpha helix. Yap may indirectly bind to SRF through MRTF-A and Tead interaction sites. FIG. 12B is a schematic diagram showing how phosphorylated ETS factors facilitate phosphorylated SRF binding to the C-FOS promoter to drive cardiomyocyte replication, while Nkx2-5 and Gata4 facilitate SRF binding to myogenic specified genes to drive cardiomyocyte differentiation. It shows the mutual inhibitory activity shared between myocyte replication and myocyte differentiation. FIG. 12C shows extracts of SRF null murine ES cells rescued by lentiviral expressed SRF triplet alanine scanning mutants, spanning the N-terminal extension to the start of alpha helix 1, were used in EMSA DNA binding assays to the [P32] labeled alpha-cardiac promoter in the presence of lentiviral expressed Gata4. FIG. 12D shows that extracts of SRF null murine ES cells rescued by lentiviral expressed SRF triplet alanine scanning mutants, spanning the N-terminal extension to the start of alpha helix 1, were used in EMSA DNA binding assays to the [P32] labeled alpha-cardiac promoter the presence of virally expressed Nkx2-5 in SRF null murine ES cells. FIG. 12E shows results of a luciferase reporter assay of viral transfected alpha cardiac actin promoter luciferase reporter with SRF mutants and virally co-expressed Gata4. FIG. 12F shows results of a luciferase reporter assay of viral transfected alpha cardiac actin promoter luciferase reporter with SRF mutants and virally co-iexpressed Nkx2-5.

FIG. 13A is a heat map of gene expression following lentiviral transfection of SRFwt and SRF153 (A3) mutant rescue of null SRF murine ES cells. Note the increased expression of stem cell marker genes and cyclins, which, however, does not support the expression of many cardiac specified genes and assembly genes needed for sarcomerogenesis. FIG. 13B shows that MADS box DNA contact sites were shown by X-ray crystal analysis. FIG. 13C shows that EMSA of expressed Nkx2-5 and or Gata4 in the context of the alpha cardiac actin promoter failed to stabilize the single alanine point mutant, Lys154Ala, as a critical base contact. FIG. 13D shows that EMSA of expressed ETS factor, Elk1, in the context of a FOS promoter, stabilized SRF (SRF154A) DNA binding revealed by the appearance of a ternary complex factors (tcf). FIG. 13E shows a schematic model of where Stemin (153 (A3)) supports cardiac myocyte replication, because Elk1 stabilized Stemin binding to C-FOS promoter due to an adjacent ETS Binding Sequence (EBS) but blocks cardiac differentiation because Nkx2-5 and Gata4 cofactors failed to facilitate SRF DNA binding to the cardiac sarcomeric actin gene.

Figures 1A, 1B, 1C:
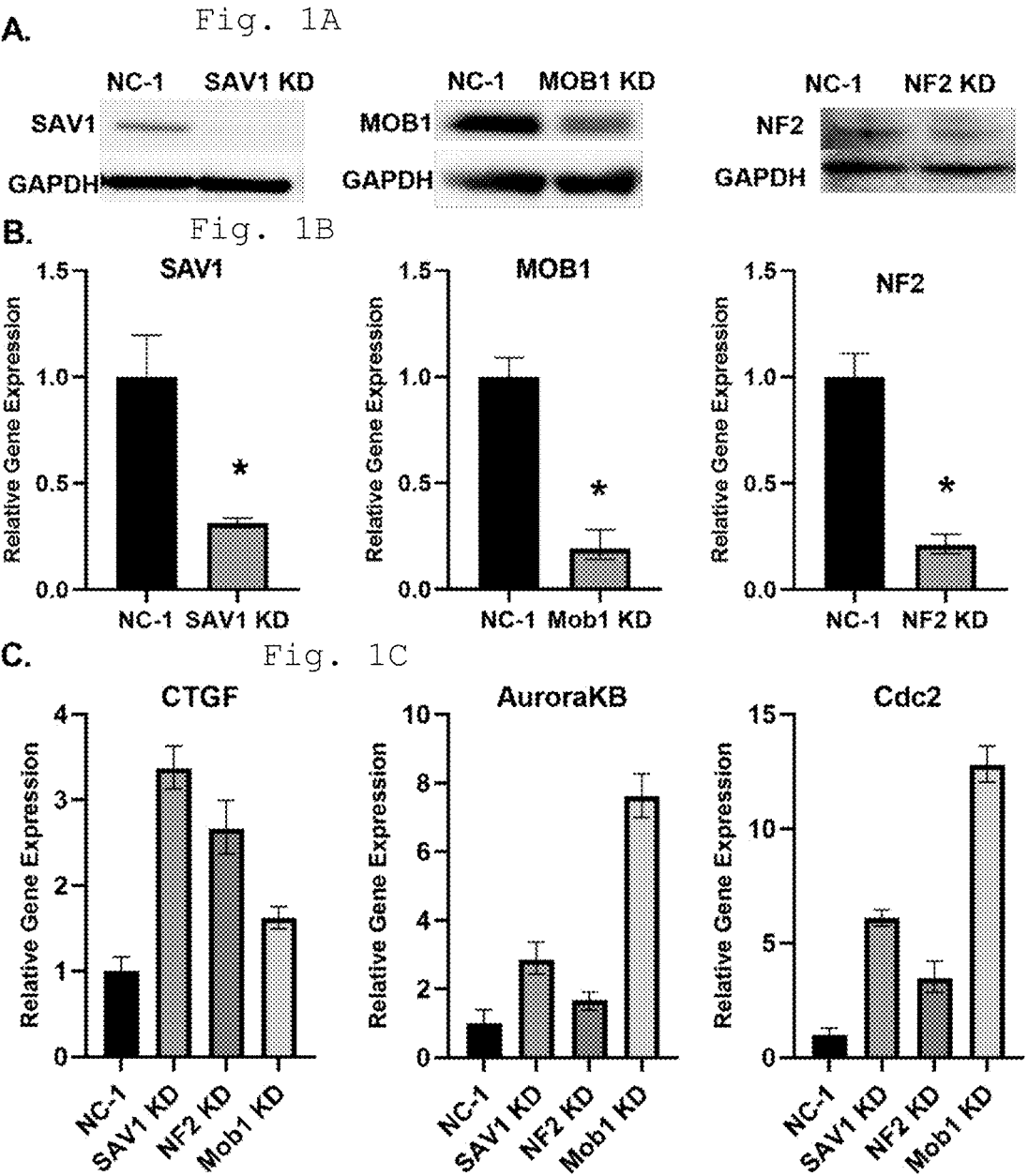
FIGS. 1A, 1B & 1C respectively show levels of knockdown of proteins SAV1, NF2, and MOB1, in H9C2 differentiated rat heart myocytes, 72 h post transfection, where transfection was with equal proportions of the DsiRNA pairs in SEQ ID NO: 1; SEQ ID NO: 2 with SEQ ID NO: 3; SEQ ID NO: 4 (for SAV1 KD); SEQ ID NO: 17; SEQ ID NO: 18 with SEQ ID NO: 19; SEQ ID NO: 20 (for NF2 KD) and SEQ ID NO: 33; SEQ ID NO: 34 with SEQ ID NO: 35; SEQ ID NO: 36 (for MOB-1 KD). NC-1 is a control DsiRNA used in the transfections. GAPDH is a ubiquitous protein whose levels are included for comparison.

TABLE OF SEQUENCES
An explanation of SEQ ID NOS: 1 to 58 is in the
SEQ ID NOS: 49 to 58 are shown. Summary section
above, where the sequences in
SEQ ID NOS: 1 to 48 are as follows.

| SEQ ID NO: 1 | ggcaacuuacuauuuggaauuacaa |
|---|---|
| SEQ ID NO: 2 | uuccguugaaugauaaaccuuaauguu |
| SEQ ID NO: 3 | auauuaugaauacaaccaugauctc |

-continued

TABLE OF SEQUENCES
An explanation of SEQ ID NOS: 1 to 58 is in the
SEQ ID NOS: 49 to 58 are shown. Summary section
above, where the sequences in
SEQ ID NOS: 1 to 48 are as follows.

| SEQ ID NO: 4 | ucuauaauacuuauguugguacuagag |
|---|---|
| SEQ ID NO: 5 | ggaaucucaugccuucauucauucg |
| SEQ ID NO: 6 | cgccuuagaguacggaaguaaguaagc |
| SEQ ID NO: 7 | cgaggugucuaagccggccgaggtg |
| SEQ ID NO: 8 | uugcuccacagauucggccggcuccac |
| SEQ ID NO: 9 | cgucguugagccggcugacuucccg |
| SEQ ID NO: 10 | ccgcagcaacucggccgacugaagggc |
| SEQ ID NO: 11 | GAUUUGGAACCUUAUUGUGAUAAAT |
| SEQ ID NO: 12 | UCCUAAACCUUGGAAUAACACUAUUUA |
| SEQ ID NO: 13 | ACUGAAAGAAAUCAGUCCCUUCUGG |
| SEQ ID NO: 14 | UUUGACUUUCUUUAGUCAGGGAAGACC |
| SEQ ID NO: 15 | CAAUUCCAAGACGAACUGAUAUCTG |
| SEQ ID NO: 16 | UUGUUAAGGUUCUGCUUGACUAUAGAC |
| SEQ ID NO: 17 | CAGUAAGGACCUGACUAGAAGCATG |
| SEQ ID NO: 18 | gugucauuccuggacugaucuucguac |
| SEQ ID NO: 19 | ccuugguacugaaacaguaagucac |
| SEQ ID NO: 20 | auggaaccaugacuuuguacauucagug |
| SEQ ID NO: 21 | gcuagaaagcagauggaaaggcagc |
| SEQ ID NO: 22 | uccgaucuuucgucuaccuuuccgucg |
| SEQ ID NO: 23 | ggaggagcuaguucaagagaucacg |
| SEQ ID NO: 24 | cuccuccucgaucaaguucucuagugc |
| SEQ ID NO: 25 | ggcugaucaguuaaagcaagacutg |
| SEQ ID NO: 26 | cuccgacuagucaauuucguucugaac |
| SEQ ID NO: 27 | AUGAGCUUCAGCUCUCUCAAGAGGA |
| SEQ ID NO: 28 | CGUACUCGAAGUCGAGAGAGUUCUUCUCCU |
| SEQ ID NO: 29 | GACAUACCAAGCUUCAACCUCAUTG |
| SEQ ID NO: 30 | GACUGUAUGGUUCGAAGUUGGAGUAAC |
| SEQ ID NO: 31 | GAAUUACUGCUUGGUACGCAGAGCA |
| SEQ ID NO: 32 | CUCUUAAUGACGAACCAUGCGUCUCGU |
| SEQ ID NO: 33 | cuucaggaacuaauugagaagcutg |
| SEQ ID NO: 34 | gugaaguccuugauuaacucuucgaac |
| SEQ ID NO: 35 | acugaagcaacugcauugaaauuca |
| SEQ ID NO: 36 | aaugacuucguugacguaacuuuaagu |
| SEQ ID NO: 37 | ggaccucaaugaauggauugcuguu |
| SEQ ID NO: 38 | ccuggaguuacuuaccuaacgacaa |
| SEQ ID NO: 39 | ggaucuaaagacagauaaauguuuc |

7

-continued

TABLE OF SEQUENCES
An explanation of SEQ ID NOS: 1 to 58 is in the
SEQ ID NOS: 49 to 58 are shown. Summary section
above, where the sequences in
SEQ ID NOS: 1 to 48 are as follows.

SEQ ID NO: 40  ccuagauuucugucuauuuacaaag

SEQ ID NO: 41  gguauggacuaaaugauaCuGACuA

SEQ ID NO: 42  ccauaccugauuuacuauGacugau

SEQ ID NO: 43  5' GCAGGUCCGAGAUAUGAAUAUCACT 3'

SEQ ID NO: 44  3' GACGUCCAGGCUCUAUACUUAUAGUGA 5'

SEQ ID NO: 45  5' GUGAUAGUUUCCGAGUAAGACCUTA 3'

SEQ ID NO: 46  3' CACACUAUCAAAGGCUCAUUCUGGAAU 5'

SEQ ID NO: 47  5' CAAAGACUAUUCUAAAGCGUCUGTT 3'

SEQ ID NO: 48  5' CCGUUUCUGAUAAGAUUUCGCAGACAA 3'

The following sequences show the primers used in determining protein levels in the experiments shown in some of the figures.

SEQ ID NOS: 59; 60 are respectively the forward and reverse primers used to monitor mouse SAV1 gene expression.

SEQ ID NO: 59 CTGTCCCGCAAGAAAACCAAA

SEQ ID NO: 60 AATGAAGGCATGAGATTCCGC

SEQ ID NOS. 61; 62 are respectively the forward and reverse primers used to monitor mouse NF2 gene expression.

SEQ ID NO: 61 GCCATCGCTTCTCGCATGA

SEQ ID NO: 62 CGCAGTTGAACTCCATCTCGG

SEQ ID NOS. 63; 64 are respectively the forward and reverse primers used to monitor mouse MOB1 gene expression.

SEQ ID NO: 63 GGCAGGTCCCAGGTATGAATA

SEQ ID NO: 64 TCAAGCTGATCCTGAACCCAA

Figures 7A, 7B, 7C, 7D, 7E, 7F, 7G, 7H, 7I:
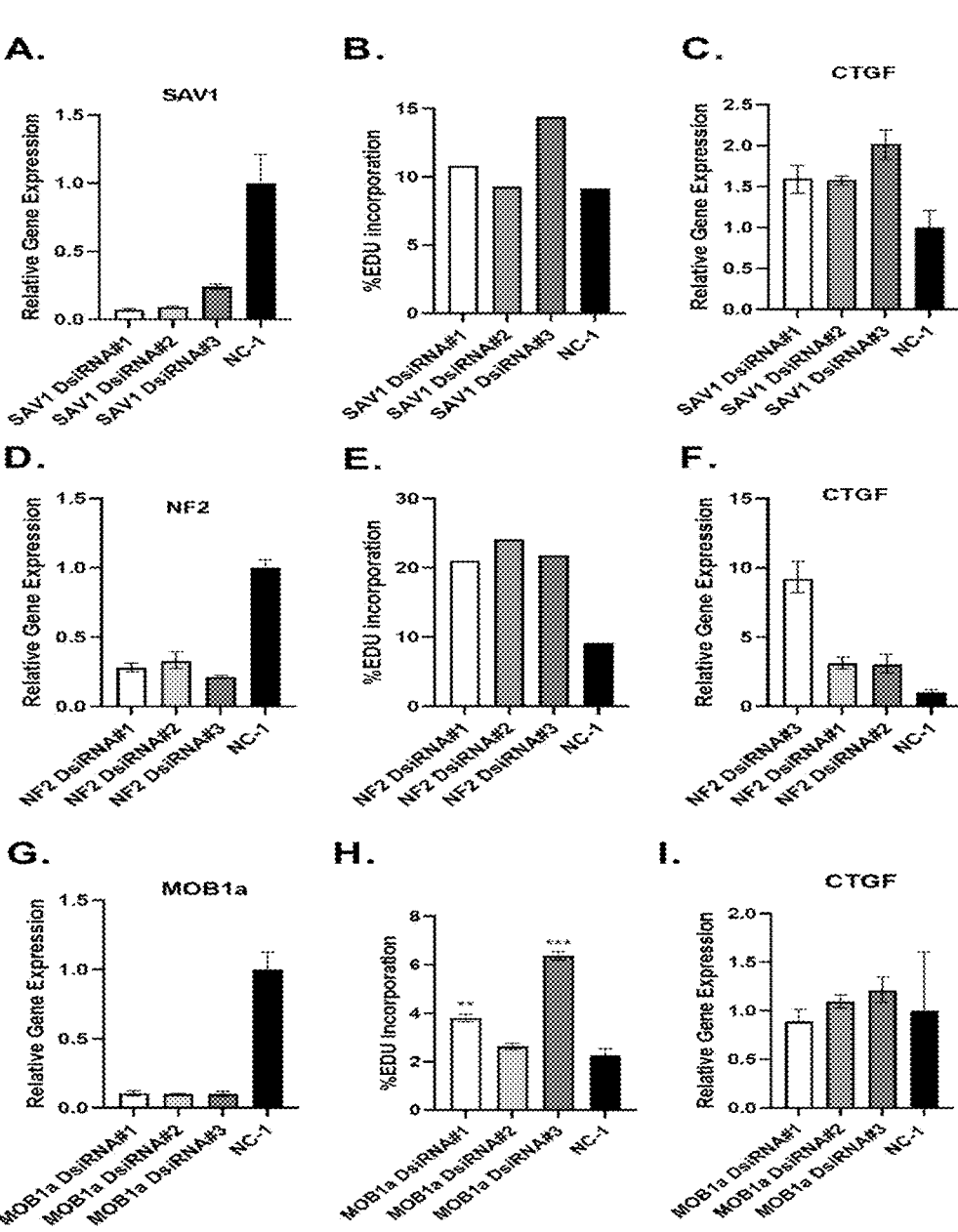

SEQ ID NOS. 65; 66 are respectively the forward and reverse primers used to monitor mouse CTGF gene expression (FIGS. 7C; 7F; 7I)

SEQ ID NO: 65 CAAGGACCGCACAGCAGTT

SEQ ID NO: 66 AGAACAGGCGCTCCACTCTG

Figures 4A, 4B, 4C:
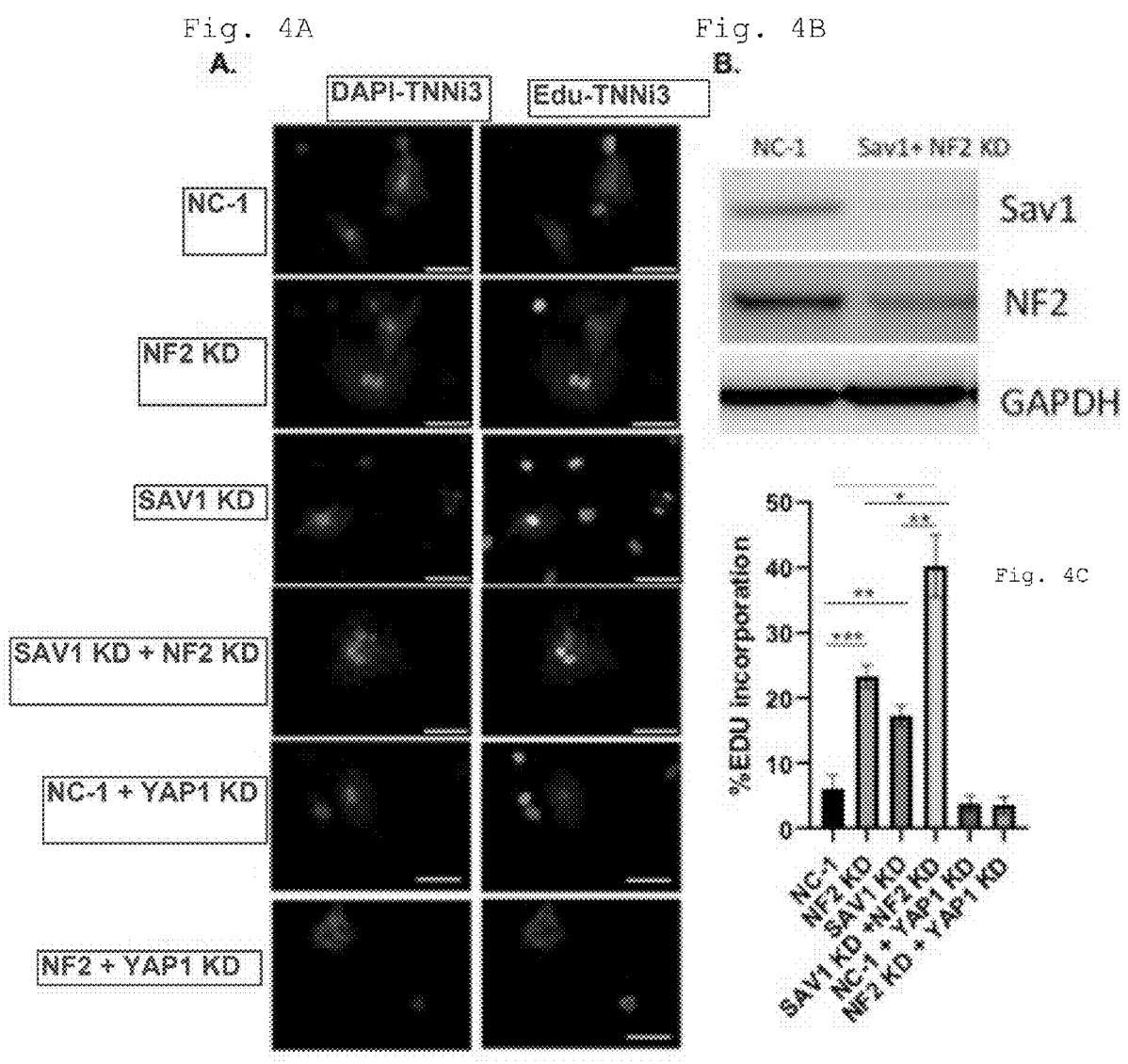
FIGS. 4A, 4B & 4C show the effect of DsiRNAs for the inhibitory proteins, the control NC-1, and a combination with YAP1, DsiRNA knockdnown, on rat neonatal cardiomyocyte proliferation 72 h post transfection.

SEQ ID NOS. 67; 68 are respectively the forward and reverse primers used to monitor mouse GAPDH gene expression (FIG. 4B).

SEQ ID NO: 67 AGGTCGGTGTGAACGGATTTG

SEQ ID NO: 68 TGTAGACCATGTAGTTGAGGTCA

SEQ ID NOS. 69; 70 are respectively the forward and reverse primers used to monitor rat Aurkb.

SEQ ID NO: 69 ATGAGCAGCGGACTGCCACG

SEQ ID NO: 70 GTCCAGGGTGCCGCACATGG

SEQ ID NOS. 71; 72 are respectively the forward and reverse primers used to monitor rat Cena2 (FIG. 6B).

SEQ ID NO: 71 CCCGGAGCCAGAAAACCACTGGT

SEQ ID NO: 72 GTCCACAAGGATGGCCCGCAT

SEQ ID NOS. 73; 74 are respectively the forward and reverse primers used to monitor rat Cdc20.

SEQ ID NO: 73 GGCTGGGTTCCCCTGCAGACAT

SEQ ID NO: 74 TGGGCAAAGCCATGGCCTGAGA

SEQ ID NOS. 75; 76 are respectively the forward and reverse primers used to monitor rat Cdc2.

SEQ ID NO: 75 TTTCGGCCTTGCCAGAGCGTT

SEQ ID NO: 76 GTGGAGTAGCGAGCCGAGCC

8

The primers for the following genes were purchased from IDT Technology (Newark, NJ)

GAPDH (sequence name: Rn.PT.39a.11180736.g);
NF2 (sequence name: Rn.PT.58.35891527);
YAP1 (sequence name: Rn.PT.58.10413179);
SAV1 (sequence name: Rn.PT.58.37256237);
CTGF (sequence name: Rn.PT.58.37685462.g).

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Dosage and Administration

The dosage and administration regimen can be determined for humans and larger mammals by extrapolating, based on mammalian mass, the dosage and regimen required to cause cardiac cell proliferation in mice and/or rats. Various administration routes can be used to administer one or more inhibitors and mutant SRFs to subject mammals, including oral administration, inhalation, subcutaneous administration, intravenous administration, intraperitoneal administration, intramuscular administration, intrathecal injection, intra-articular administration, topical administration, central administration, peripheral administration, aerosol-based administration, nasal administration, transmucosal administration, transdermal administration, parenteral administration, and combinations thereof.

Induction of Cell Proliferation In Vitro

The compositions of the can be used to proliferate various types of cardiac cells in vitro, e.g., in a container such as a petri dish. In some embodiments, the cardiac cells are held in a scaffold, such as in a scaffold for a heart or cardiac tissue.

Additional Embodiments

Reference will now be made to more specific embodiments of the present disclosure and experimental results that provide support for such embodiments. However, Applicant notes that the disclosure below is for illustrative purposes only and is not intended to limit the scope of the claimed subject matter in any way.

The experiments described below and shown in the figures support the use of the DSiRNAs described herein for cardiac cell replication.

Materials and Methods

Cell Culture

H9C2 rat cardiomyocyte cell line was purchased from the ATCC. For proliferation, cells were maintained in DMEM/ high glucose with 2 mM Glutamax, 1 mM sodium Pyruvate, and 100 U/ml penicillin-streptomycin (ThermoFisher Scientific) supplemented with 10% Fetal Bovine Serum (Gendepot). Only cells at low passage number were used and cells were passaged before reaching 70% confluency. For differentiation, media supplemented with 1% Fetal Bovine Serum was changed every other day and 1 µM retinoic acid (Sigma-Aldrich) was added every day for a week.

NIH3t3s cells were purchased from the ATCC. Cells were maintained in DMEM/high glucose with 2 mM Glutamax, 1 mM sodium Pyruvate, and 100 U/ml penicillin-streptomycin (ThermoFisher Scientific) supplemented with 10% fetal bovine serum (Gendepot). Cells were passaged at 70% confluency. All cell types were passaged using 0.25% trypsin (ThermoFisher Scientific) before reaching confluency.

Rat neonatal cardiomyocytes were purchased from Cell Applications and maintained in the basal media supplemented with growth supplements provided by the same manufacturer according to their recommended guidelines.

DsiRNA Transfection

DsiRNA (Dicer Substrate siRNAs) RNA duplexes were purchased from IDT Technology. When H9C2 cells were used, they were plated and allowed to differentiate for 1 week. On the day of transfection, medium was changed, and cells were transfected with Lipofectamine RNAiMax following the manufacturer's guidelines (ThermoFisher Scientific). Twenty-five pmoles of DsiRNA for a 6-well format, 10 µmol for a 12-well format or 5 µmol on a 24-well format was used for all experiments. Control transfection was performed using non-targeting DsiRNA (NC-1) and transfection efficiency was checked using DsiRNA conjugated with a fluorophore Tye593 (IDT). Cells were harvested or treated as indicated for 24, 48, or 72 h post transfection. For H9C2 cells and rat neo-natal cardiomyocytes, an equal mix of respective DsiRNAs complementary pairs, as below, were used for all experiments.

Rat MOB1a: SEQ ID NOS: 33 & 34; 35 & 36;
Rat NF2: SEQ ID NOS: 17 & 18; 19 & 20;
Rat SAVI: SEQ ID NOS: 1 & 2; 3 & 4;
NC-1 (Negive Control DsiRNA).

QPCR experiments were performed in a 12-well format and samples were harvested at the indicated times. RNA was isolated using RNAeasy kit (Qiagen) following the manufacturers' guidelines. RNA concentration was determined using a Nanodrop (ThermoFisher Scientific), and then cDNA was synthesized using one microgram of total RNA and the qscript cDNA superMix reagent following the manufacturer's guidelines (Quanta Biosciences). Next, cDNA samples were diluted in water and QPCR was performed using the Power SYBER Green PCR MasterMix reagent and an Applied Biosystems 7900HT real time PCR system. All PCR primer sequences are provided in the supplemental methods.

The relative gene expression was estimated using the comparative Ct method. The relative Ct value of an mRNA transcript was calculated first by subtracting the Ct value of the housekeeping gene GAPDH from the mRNA Ct value of the gene of interest. The relative Ct values were normalized to non-transfected cells to determine the fold-change in gene expression. Statistical significance was determined by performing unpaired t-tests between untreated and treated samples.

Western Blot

Western Blot samples were collected from a 6-well format. Samples were harvested 72 h after transfection. Cells were rinsed with PBS and scraped in RIPA buffer (Genedepot) with antiprotease and anti-phosphatase cocktail (ThermoFisher Scientific). Protein concentration was determined using a BCA protein assay (ThermoFisher Scientific) according to the manufacturer's guidelines. The same protein amount for each sample was loaded on a Nupage 10% bis-tris electrophoresis gel and transferred to a PVDF membrane. Membrane was washed with TBS buffer with 0.1% Tween 20 (TBST) then blocked in 5% bovine serum albumin for 1 h. at room temperature. Primary antibodies (Anti-MOB1 (1:1000) (Cell Signaling 13730S); Anti-SAV1 (1:1000) (Cell Signaling 3507) and anti-NF2 (1:1000) (Abcam Ab88957) were added and incubated overnight at 4° C. Membranes were then washed with TBST and secondary HRP antibody was added (anti-rabbit Cell Signaling #7074; anti-mouse Cell Signaling #7076) at 1:10000 for 1 h. at room temperature. After washing with TBST, the membrane was developed using Pierce ECL western blotting substrate (ThermoFisher Scientific). Membranes were stripped using western blot restore PLUS western blot stripping buffer (ThermoFisher Scientific). Membranes were then incubated with rabbit anti-GAPDH conjugated with HRP (Santa Cruz Biotechnology) overnight in 5% milk followed by washing and detection with the same western blotting substrate.

EdU Flow Cytometry

Cells were plated in 6-well format and transfected as previously described. Cells were lifted using trypsin and the trypsin action was stopped by the addition of medium with serum. The samples were centrifuged, washed with PBS with 1% BSA to prevent cells from clumping. Cells were then fixed and permeabilized with ice-cold 100% methanol while being gently vortexed then incubated on ice for 30 min. Excess PBS was then added, and samples were centrifuged and washed with PBS twice. Edu reaction was performed according to the manufacturer's instructions using the Click-it EdU Alexa Fluor flow cytometry assay kit (ThermoFisher Scientific).

After Edu reaction, cells were washed in PBS, then DNase-free RNAse A (Thermo Scientific) was added at a final concentration of 0.2 mg/ml, then propidium iodide (Invitrogen) was added at a concentration of 3 µM. Samples were analyzed using a BD LSR II flow cytometer (BD Biosciences).

EdU and Immunostaining Assay

Cells were plated on 0.1% gelatin coated coverslips in 24-well format. Cells were transfected like described previously. Medium was changed after 24 h and 10 µM of Edu was added. 48 h after transfection, 10 µM Edu were added and 6 h later cells were fixed. Cells were washed in PBS then fixed in 4% Paraformaldehyde in PBS for 10 min. Edu reaction was performed according the manufacturer's instructions using the Click-it EdU Alexa Fluor™ Imaging Kit (ThermoFisher Scientific). Additional staining for cardiac markers was performed with the primary antibodies (Anti-heavy chain cardiac myosin antibody [BA-G5] (Abcam: ab50967); anti cardiac-Troponin T [1C11] (Abcam ab8295) 1:200) diluted in 1% bovine serum albumin overnight at 4° C. Cells were washed with PBS, then incubated with secondary Fluorescent Antibodies Alexa goat anti-rabbit or anti-mouse (ThermoFisher Scientific) for 1 h at room temperature in dark conditions (1:250). Finally, the coverslips were washed with PBS with Hoechst 33342 and mounted with slow-fade mounting medium (ThermoFisher Scientific). Images were captured with Nikon Eclipse Ti microscope.

Mitosis Detection on Rat Neonatal Cardiomyocytes

Cells were fixed using 4% formaldehyde in PBS for 10 min, then washed with PBS. Fixed cells were permeabilized with 0.25% tritonX-100 in PBS for 15 min, then washed with PBS. Samples were incubated with image-it FX signal Enhancer for 30 min before washing with PBS. Samples were blocked with 5% BSA in PBS for 1 h at room temperature. Mitosis was detected using the Rabbit phospho-histone 3 H3 (Ser10) Antibody mitosis marker (Sigma-Aldrich 06-570) (1:200). Cardiac marker troponin Tnni3 was detected using the mouse anti-troponin T (ab8295 Abcam) (1:250). Both primary antibodies were diluted in 1% BSA in PBS and samples were incubated overnight at 4° C. After washes, secondary antibodies (Alexa Fluor goat anti-rabbit 488, Alexa Fluor goat anti-mouse 647 (ThermoFisher Scientific) both at 1:250 in PBS+1% BSA) were added for 1 h at room temperature under dark conditions. Samples were then washed and incubated with Hoechst 33342 to stain the nucleus. Nikon Ti eclipse epi-fluorescence microscope was used for capturing the images.

Live Cell Imaging

H9C2 Cells were plated in a 24-well plate and differentiated for 10 days. Cells were transfected with DsiRNAs. The samples were incubated in the Incucyte S3 Live-Cell Analysis System using the 20× objective. The instrument was set to take a picture every hour of each well at 16 different locations for a period of 48 h. Cell confluence was measured and plotted using the Incucyte Zoom (Sartorius) software.

Rat primary neonatal cardiomyocytes were purchased in a 12 well plate from Cell Applications. Cells were co-transfected with 400 ng of ES FUCCI which was a gift from Pierre Neveu (Addgene plasmid #62451) (10) and DsiRNAs like described above, using Jetprime transfection reagent according to the manufacturer's guidelines. Cells were then incubated in the Incucyte S3 Live-Cell Analysis System (Sartorius) under regular cell culture conditions. The instrument was set to take a picture every hour of each well at 16 different locations using a 10× objective for 48 h. Image analysis was performed using the Incucyte software analysis tool.

RNA-Sequencing Assay

Rat neonatal cardiomyocytes plated on a 12-well plate were treated with 10 pmols of DsiRNAs using Lipofectamine RNAimax. Forty-eight h post transfection, cell lysates were harvested. RNA was extracted using RNeasy Mini Kit (Qiagen) with on-column RNase-Free DNase (Qiagen) digestion following manufacturer's instructions. Extracted RNA samples underwent quality control assessment using the RNA tape on Tapestation 4200 (Agilent) and were quantified with Qubit fluorometer (Thermo Fisher). The RNA libraries were prepared and sequenced at the University of Houston Seq-N-Edit Core per standard protocols. RNA libraries were prepared with QIAseq Stranded Total RNA library Kit (Qiagen) using 100 ng input RNA. Ribosomal RNA was depleted with QIAseq FastSelect HMR kit (Qiagen). RNA was fragmented, reversetranscribed into cDNA, and ligated with Illumina sequencing adaptors at the 5' and 3' ends. The size selection for libraries was performed using SPRIselect beads (Beckman Coulter) and purity of the libraries was analyzed using the high sensitivity DNA 1000 tape on the Tapestation 4200 (Agilent) with a size of 300 bps. The prepared libraries were pooled and sequenced using NextSeq 500 (Illumina); generating ~15 million 2×76 bp paired-end reads per samples.

For data analysis, trimGalore! was used to control the quality of the data, followed by alignment to the rat genome (Rn6 from ENSEMBL) using the STAR aligner. The limma/voom R-package was used to perform the differential gene analysis. Batch correction was performed using the SVA R-package followed by differential gene analysis using the limma/voom R-package. Pathway analysis was performed against a collection of rat-specific GO/KEGG pathways from the Ge lab using GSEA v3.0.

Luciferase Assay

NIH3t3 cells were plated at the indicated cell density on white opaque 96-well culture plates and transfected the same day with the YAP-TEAD-driven 8×GTIIC-firefly luciferase (Addgene plasmid #34615) (35). The pRL SV40 renilla luciferase (Promega) was also co-transfected for data normalization. Effectene (Qiagen) or lipofectamine 3000 were used to transfect 50 ng of each reporter according to the manufacturers' guidelines.

One pmole of siRNAs per well was transfected 24 h later using Lipofectamine RNAiMax, following the manufacturer's guidelines (ThermoFisher Scientific). Cells were incubated overnight before measuring the luciferase activity using the Dual-Glo luciferase assay system (Promega) with the infinite 200Pro Tecan plate reader. Statistical significance was determined by comparing the mean of the relative fluorescence unit (RFU) of treated samples to untreated control samples using an unpaired t test.

Results of SAV1, NF2, and MOB1 DsiRNAs Knockdown Experiments

Hippo Pathway knockdowns stimulate cell proliferation in mouse fibroblasts. NIH3t3 mouse fibroblast cells were transfected with 3 different SAV1 KD, NF2 KD, and MOB1 KD DsiRNAs and the gene silencing was verified with RT-PCR. All tested DsiRNAs were effective in reducing SAV1, NF2 and MOB1 transcript levels (FIGS. 7A to 7I). Their efficiency was then tested in inducing cell proliferation and driving YAP-TEAD target genes. Different SAV1 DsiRNAs had a variable and relatively low efficiency of stimulating cellular proliferation as tested by a flow cytometry EdU incorporation assay (c & 7H) which indicates de novo DNA synthesis. Cells were transfected with a dual-luciferase reporter system where the firefly luciferase expression level is controlled by a YAP-TEAD synthetic promoter and a control promoter drives renilla luciferase expression for data normalization. SAV1-knockdown cells showed an increase in luciferase activity (FIGS. 8A, 8B).

Similar experiments were run to test NF2 DsiRNAs and their effect on YAP activity and proliferation on NIH3t3 cells. NF2 transcript levels decreased with all NF2 DsiRNAs tested (FIG. 7D) and overall, they were more effective than SAV1 DsiRNAs in stimulating cellular proliferation (FIG. 7E). The CTGF level also increased, and DsiRNA was particularly efficient (FIG. 7F). Finally, the cells were tested with a YAP-TEAD reporter luciferase assay, and cells with NF2 knockdown exhibited an increase in YAP activity (FIGS. 8A, 8B). These findings support the idea of stimulating cellular proliferation of mouse fibroblasts with SAV1 and NF2 knockdowns. Similarly, MOB1 knockdown with the screened DsiRNA was effective and promoted cellular proliferation (FIG. 7H). However, CTGF levels following MOB1 KD did not significantly increase (FIG. 7I). This preliminary data supports that SAV1 KD, NF2 KD and MOB1 KD DsiRNAs can efficiently silence the target genes and can enhance cell proliferation in mouse fibroblasts.

It was also investigated whether inhibiting the interaction between MOB1 and MST kinase could be beneficial for cell proliferation. MOB1 acts as a kinase activator for both LATS and MST. It was hypothesized that blocking the interaction between MOB1 and MST kinase can inhibit the Hippo pathway by inactivating its core kinases. The interaction of several MST-derived peptides of different lengths with MOB1 has been described. A peptide derived from MST2 kinase was overexpressed: the MOB1 binding domain (MBD) in NIH3T3 cells and confirmed the overexpression of the MBD peptide with RT-PCR (FIG. 9B). Consistent with MOB1 knock-down results (FIG. 7H), cells transduced with a lentivirus expressing MBD peptide also induced novel DNA synthesis measured by EdU incorporation in mouse NIH3t3 cell line (FIG. 9A). The data proves the possibility of inducing an active cellular replication by specifically targeting MOB1-MST1/2 kinase interaction using a peptide.

Knockdowns of Hippo Pathway Regulators in Rat Cardiac-Like Cells H9C2

After confirming that DsiRNAs can promote cell proliferation of mouse fibroblasts, the study moved into cells with more cardiac-like properties, the H9C2 rat myoblast cell line. H9C2 cells were differentiated for a week and cultured in low serum medium supplemented with retinoic acid. Cells were transfected with NF2, MOB1 and SAV1 rat DsiRNAs. Reduced proteins levels due to gene silencing were checked with western blot. All three protein levels decreased as compared to the control (FIG. 1A). The transcript levels of each of the three proteins decreased as demonstrated by q-PCR (FIG. 1B) and the level of YAP target gene CTGF increased as a result of such gene silencing (FIG. 1C). Although MOB1 KD did not efficiently increase the CTGF level, it was more potent than NF2 and SAV1 in increasing the transcript levels of cell cycle genes Aurora kinase B and CDC2 (FIG. 1C). This indicates that MOB1 silencing has the potential to be more efficient than silencing of SAV1 and NF2 in inducing heart cell regeneration. This data supports that using DsiRNAs of Hippo regulators NF2, SAV1 and MOB1 can successfully reduce their transcript and protein levels and lead to the reactivation of the cell cycle.

Figure 2A:
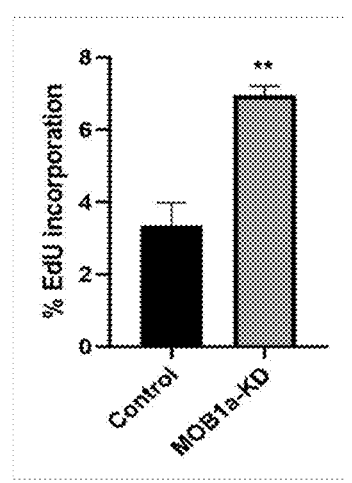
FIGS. 2A, 2B show the knockdown in H9C2 differentiated rat heart myocytes, 72 h post transfection, where transfection was with equal proportions of the DsiRNA pairs in SEQ ID NO: 33; SEQ ID NO: 34 with SEQ ID NO: 35; SEQ ID NO: 36 (for MOB-1 KD). Data is a representation of three independent experiments. Error bars represent the standard error of the mean. "**" indicates a statistically significant difference between the treatment and the control (P<0.01). Scale bar represents 100 microns where knockdown of MOB1 is measured by an Edu reaction and assay.
Figure 2B:
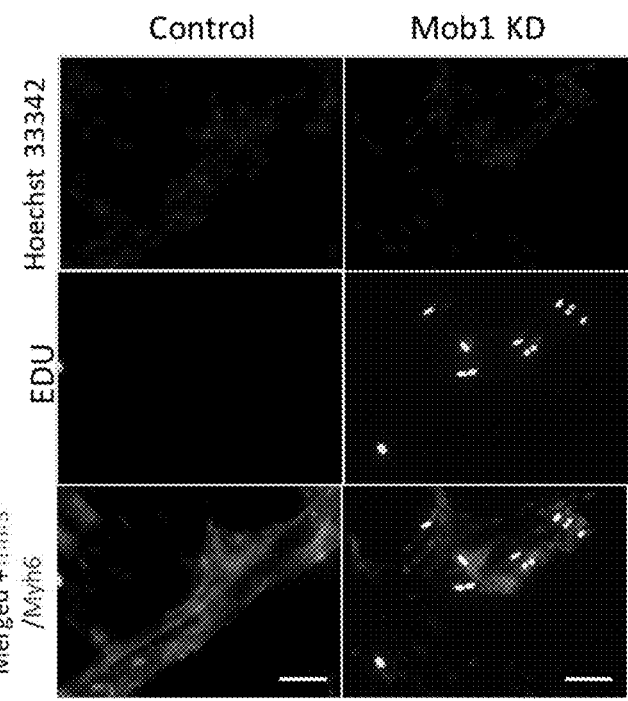
Figure 3:
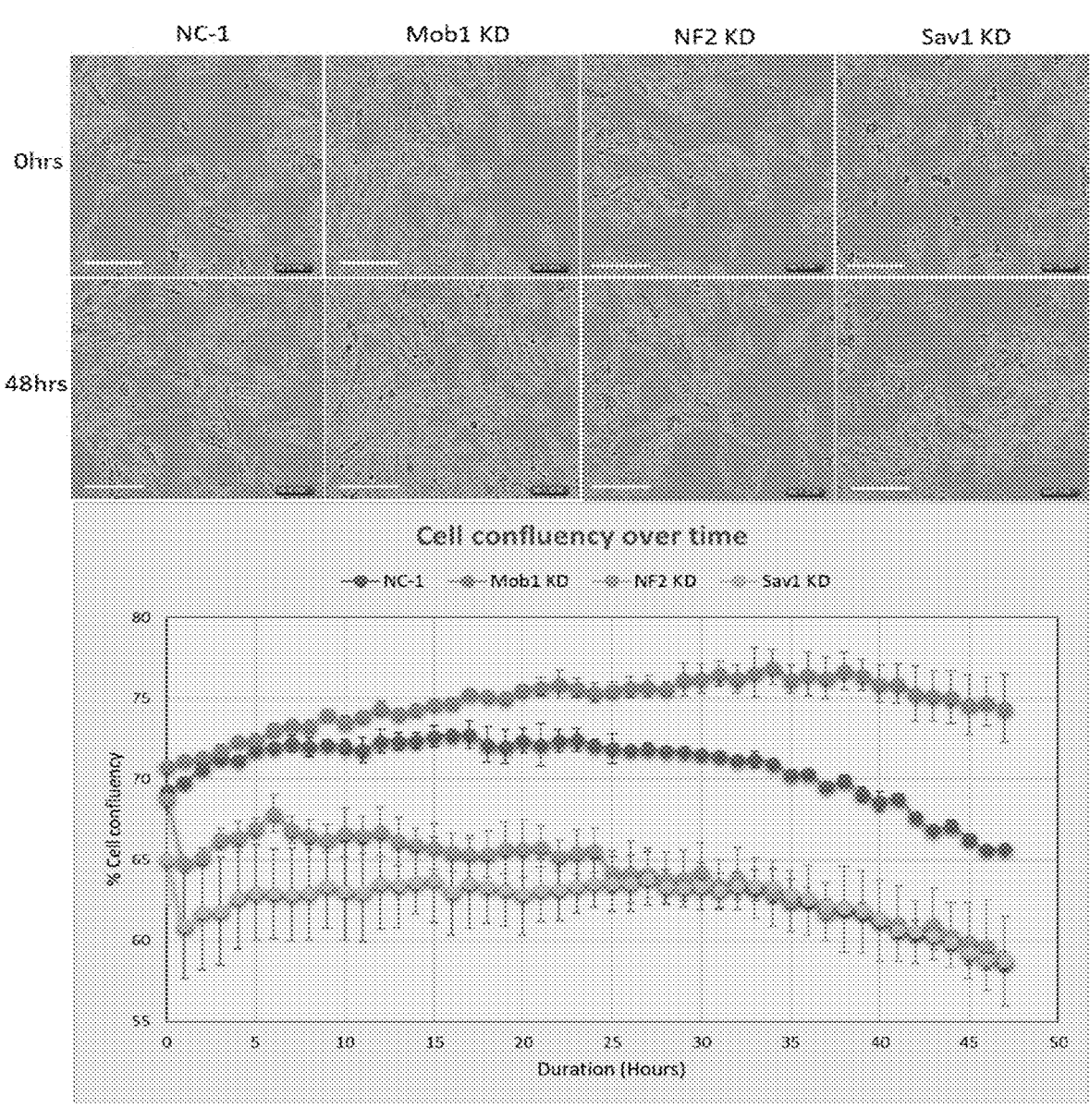
FIG. 3 shows the effect of knockdown by the DsiRNAs and proportions as in FIGS. 1A, 1B & 1C, i.e., to knockdown SAV1, MOB1 and NF2, as well as on NC-1, on rat primary neonatal cardiomyocyte confluence.

Knocking down MOB1 was then tested in differentiated H9C2 for proliferation using an EdU incorporation assays. In both flow cytometry and immunostaining assays, MOB1 knockdown significantly induced de novo DNA synthesis, which indicates cell proliferation (FIG. 2A, 2B). The efficiency of NF2, SAV1 and MOB1 knockdown as compared with inducing cell H9C2 proliferation over 48 h using live cell imaging. Cell confluency increased over time more importantly in MOB1 KD cells than in the control, NF2 KD or SAV1 KD cells (FIG. 3). This data also suggests that MOB1 silencing may be more potent that NF2 and SAV1 in inducing cell proliferation.

Knockdowns of Hippo Pathway Regulators in Rat Neonatal Cardiomyocytes

Rat neonatal cardiomyocytes were treated with DsiRNAs for 72 h and pulsed twice with EdU to capture de novo DNA synthesis, which indicates cell proliferation. Both NF2 and SAV1 single knockdowns significantly increased cardiac cells proliferation (FIGS. 4A, 4B). This effect disappears when YAP is silenced. This demonstrates that the observed cardiomyocyte proliferation effect is driven in a YAP-dependent way (Hippo signaling inactivation). Interestingly, neonatal cardiomyocyte proliferation was significantly more pronounced when combining SAV1 and NF2 gene silencing compared to silencing each gene individually.

Figures 5A, 5B:
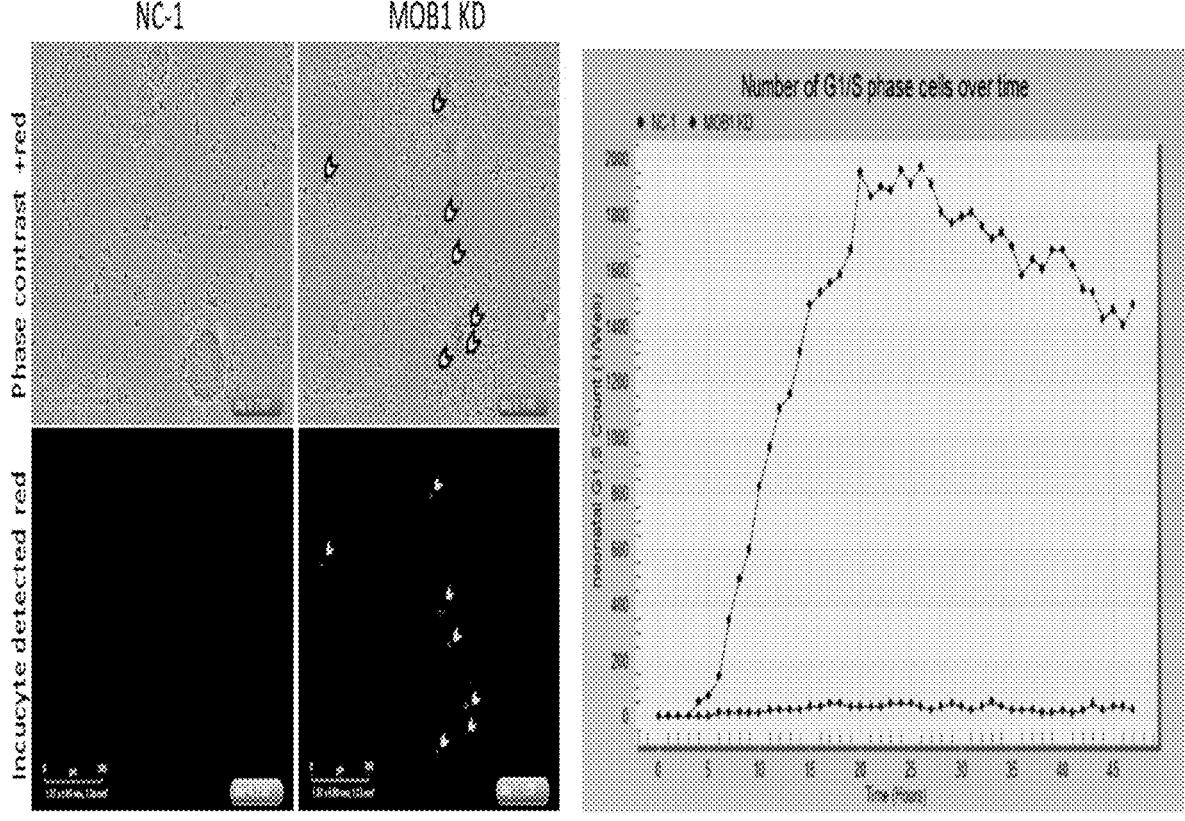
FIGS. 5A, 5B show live cell imaging of rat neonatal cardiomyocytes transfected with the cell cycle ESFUCCI system combined with equal proportions of MOB1 KD DsiRNAs (SEQ ID NO: 33; SEQ ID NO: 34 with SEQ ID NO: 35; SEQ ID NO: 36) or control (NC-1 KD) over 48 h. MOB1 KD increases the number of cells reentering the cell cycle as detected by the number of red nuclei (objects). Select images of the three treatments 48 h post transfection show cells in G1/S phase (as plotted in FIG. 5B) and their detection by the live cell imaging system (Incucyte). Yellow arrows indicate cells in G1/S phase. Scale bars represent 300 microns.
Figure 10:
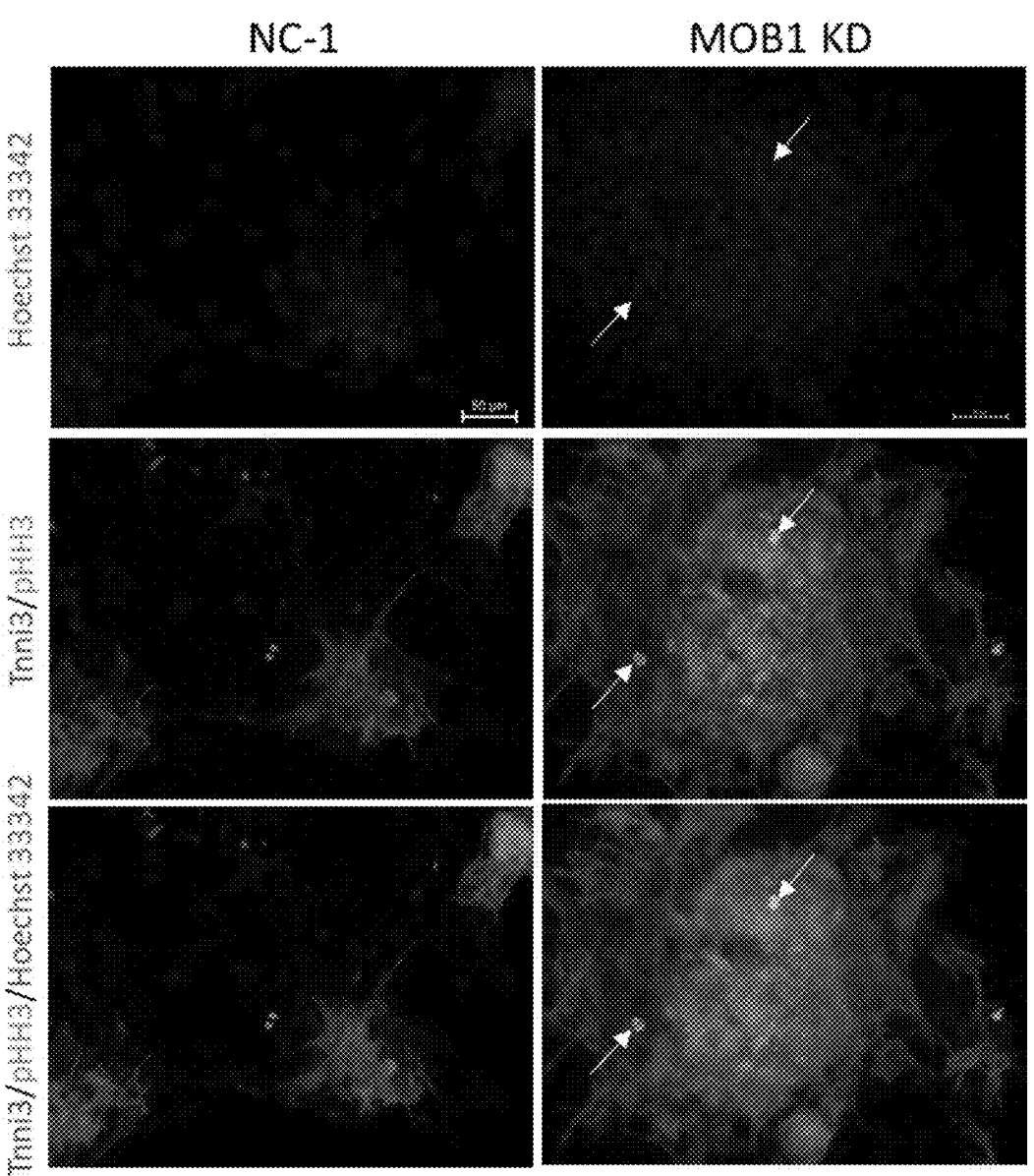
FIG. 10 shows immunofluorescence imaging representations of mitosis by immunostaining with a mitosis marker (phospho-Histone H3 phH3 positive), in control and MOB1 KD rat neonatal cardiomyocytes. Arrows are pointing at cells (Troponin Tnni3 positive) undergoing mitosis. Scale bars represent 50 microns.
Figure 11:
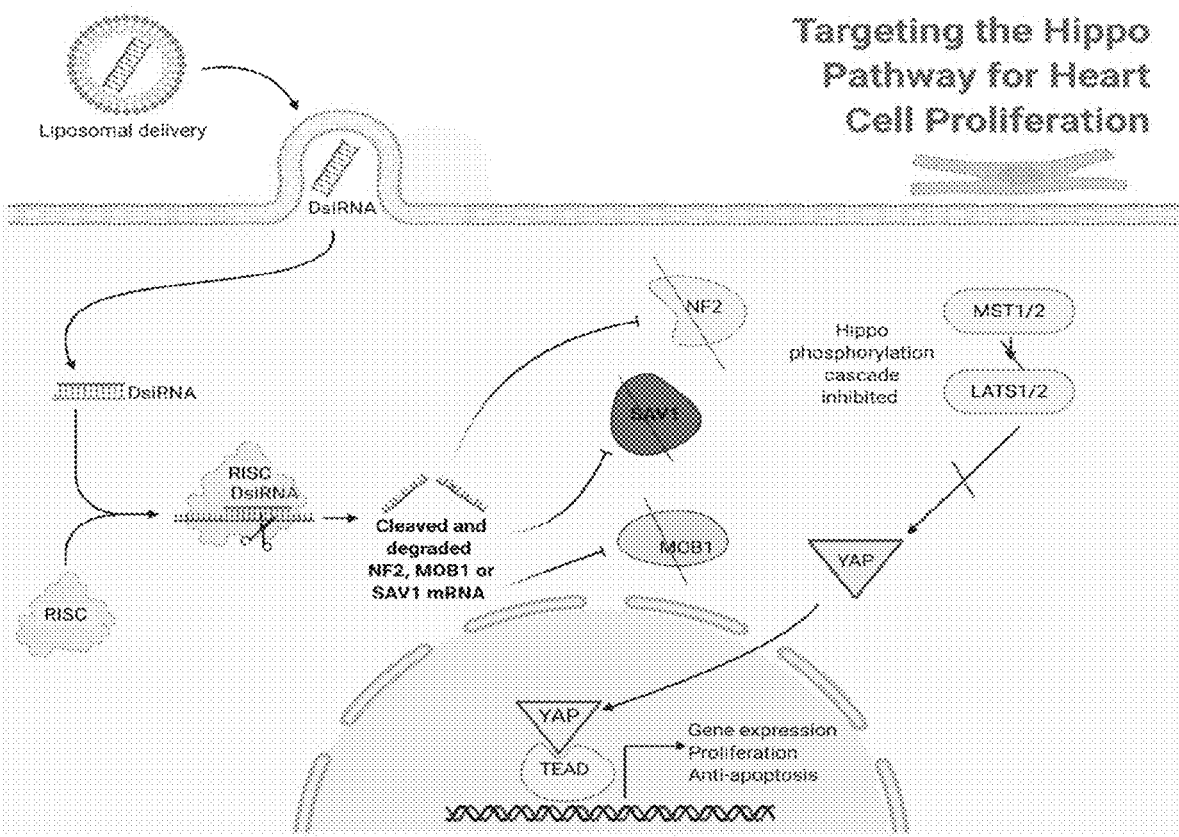
FIG. 11 illustrates manipulating the Hippo pathway to induce cardiac cell proliferation.

Next, the effect of MOB1 knockdown was investigated on rat neonatal cardiomyocytes using live cell imaging. To follow the cell cycle status of the cells, the cells were co-transfected with DsiRNA and a plasmid DNA containing a cell sensor system (ES-FUCCI) (Addgene plasmid #62451). The FUCCI (Fluorescence Ubiquitination-based cell cycle indicator) system allows the visualization of the cell cycle using a fusion of fluorescent proteins conjugated with a portion of Geminin and Cdt1. Ubiquitination of Geminin and Cdt1 by E3 ligases leads to their degradation by the proteasome. E3 ligases activity is modulated by the cell cycle phase. In short, the system makes the nucleus appear red fluorescent during G1 and beginning of S phase (Geminin degraded), and green fluorescent during S, G2 and M phases (Cdt1 degraded). Silencing MOB1 with this system was tested. In a span of 48 h there was an increase of G1/S phase in MOB1 KD cells as compared to the control (FIGS. 5A, 5B). A transition to G2/M phase (green fluorescence) in 48 h post transfection was not observed, and an extended time may be necessary. The effect observed by immunostaining was confirmed with a mitosis marker (phospho-Histone 3 (ser10)). FIG. 10. Using coding RNA sequencing, the effect of knocking down MOB1 on primary rat neonatal cardiomyocytes was investigated in comparison to NF2 KD and SAV1 KD on primary rat neonatal cardiomyocytes after 48 h of treatment. All three gene transcript levels decreased significantly. MOB1 knockdown showed the clearest and highest levels of enrichments for pathways linked to cell division (FIG. 6A; FIG. 6B).

NF2 and SAV1 knockdowns show enrichments mainly for protein synthesis and organelle developments, and less enrichment for cell cycle related genes. MOB1 silencing resulted in the increase of the level of genes covering DNA replication, chromosome segregation, and all cell cycle phases and transitions (FIG. 6B). These upregulated cell cycle genes include cdk1 (13), cdc6 (14) ccna2 (15), ccne2 (16) (FIG. 6B).

Upon MOB1-knockdown treatments, a downregulation of the cardiomyocyte differentiation and contraction was observed (FIG. 6C). This process was described previously as part of the process for cardiac proliferation in different organisms, where terminally differentiated cells dedifferentiate first before undergoing cell division. Another observation is that, at least using DsiRNAs, MOB1 silencing makes cell division occur faster than NF2 and Sav1 Knockdowns. Other downregulated pathways in MOB1 knockdowns include cell junction, cell migration and the cytoskeleton (FIG. 6A).

Mutant SRF For Enhanced Cardiac Cell Proliferation

SRF is a member of an ancient DNA binding protein family that shares a highly conserved DNA-binding/dimerization domain of 90 amino acids termed the MADS box shown schematically in FIG. 1A. MADS boxes have similar DNA binding specificities and dimerize to symmetrically contact the serum response element with a consensus sequence CC (A/T) 6GG, also known as the SRE and or CArG box. The appearance and diversification of nascent embryonic cardiac and smooth muscle cells require the combinatorial interactions of SRF with other transcription factors, enriched in the early progenitor cells. Also, a feature of a large number of cardiac and virtually all of the smooth muscle-expressed genes to date is their dependence upon CArG boxes. Mutations that prevent SRF binding severely impair the expression of c-fos, as well as muscle-restricted genes. An Ets factor, such as ELK1 contains an interactive B box and stabilizes SRF binding to DNA, especially in the presence of an adjacent ETS site.

In addition, CArG boxes recruit SRF and cofactors, such as Nkx2-5, and Gata4, that strongly enhance SRF-DNA binding affinity; thus, permitting the formation of higher-order DNA binding complexes at relatively low SRF input. Similarly, CArG boxes recruit the cysteine-rich protein 2 LIM protein, which bridges SRF and GATA6 factors through interaction with the MADS N-terminal extension and myocardin, which competes with Ets factors that interact with the loop region of the MADS box shown in FIG. 1A. All of these myogenic cofactors greatly enhance SRF transactivation.

Disruption of Nkx2-5 and Gata4 co-interactions with SRF blocks cardiac differentiation gene programs. The interaction with Nkx2-5 and Gata4 was disrupted by generating alanine scanning mutations across the SRF N-terminus up to the alpha I helix of the SRF's MADS box. FIG. 1A shows a schematic diagram of the MADS box domain binding to DNA. Site-directed PCR mutagenesis was used to create amino acid substituted mutations at specified residues across the SRF core domain. Residues were changed to alanines (giving a neutral charge and removing potential interacting side chains), as shown in FIG. 1B. An SRF mutant was identified, named Stemin, that no longer recognizes CArG boxes, nor is influenced by Nkx2-5 and Gata4 interactions. Thus, Stemin functions as a new synthetic transfactor that blocks cardiac differentiation and sarcomerogenesis.

Stemin is drawn to other DNA binding targets that activate cell proliferation. An excellent example is the ETS factors, as previously mentioned. Other mediators of SRF cell signaling are the myocardin related transcription factors (MRTF's MADS boxes; also known as MAL or MKL which provide the link between RhoA-dependent cytoskeletal regulation and SRF-dependent gene expression. TEAD, a critical YAP cofactor also associates with MRTF-A overlapping the myocardin binding site on the SRF's MADS box leading to rho kinase activation and cell replication. TEAD was shown to also directly binds to the MADS box independent of MRTF-A. Recently, manipulating the Hippo pathway has attracted interest, as a strategy for increasing cardiac regeneration. Cardiac-specific KO of Sav1, Lats1/2, and Nf2 genes in mature cardiomyocytes revealed enhanced cardiomyocyte proliferation, and reduced scar formation post-MI. Human YAP1 contains five phosphorylation HXRXXS motifs. Previously, YAP was mutated by replacing individual serine residues in the HXRXXS motifs with alanine, generating YAP5SA mutant (aka YAP1) that resides in the nucleus. See U.S. Pat. No. 11,179,479 B2 (incorporated by reference). Central to the Hippo pathway is a cascade of phosphorylation events in which phosphorylation of YAP1 prevents shuttling of YAP1 into the nucleus, promotes 14-3-3 binding, and protein degradation. When the Hippo pathway is inactivated, unphosphorylated YAP1 enters the nucleus and binds to multiple transcription factors (e.g., TEAD/TEF and MRTF-A). YAP1 binding to its partners TEAD and MRTF-A in the nucleus typically promotes gene expression programs that favor proliferation. Even though previous study showed YAP and SRF don't interact directly, Stemin caused myocytes to dedifferentiate and then complemented mutant YAP to induce proliferation of myocytes.

Since, Si RNA knockdowns of Sal1, NF (Merlin) and MOB1 allow YAP to enter myocyte nuclei, just like the YAP5SA mutant, it's likely that the addition of Stemin mmRNA with Si knockdowns of Sal, NF (Merlin) and MOB1 will also act in a complementary manner to favor increased cardiac myocyte proliferation.

SRF Mutants that Drive the Expression of Stem Cell Marker Genes and Blocks Cardiomyocyte-Specified Genes.

Lentivirus Production

HEK293T human kidney cells (ATCC #CRL-11268) were used as the host for lentiviral production. psPAX2 (Addgene plasmid #12260) was used as a lentiviral packaging plasmid. pMD2.G (Addgene plasmid #12259) was used as the lentiviral envelope expression plasmid. HEK293T were seeded at 30-40% confluency in a 10-cm cell culture dish. For MOB binding Domain MBD peptide overexpression, a pLenti-MBD-Puro construct, was used to produce lentiviruses. 10 ug of pLenti-MBD-Puro were mixed with 5 ug of psPAX and 5 ug of pMD2.G plasmids. The mixture was transfected the day after using Fugene HD according to the manufacturer instructions. Medium was changed 24 h after transfection. The lentiviruses were collected 72 h after transfection by collecting the medium and filtrating with 0.45-μm filters.

Demonstrating SRF Mutant Activity

Figures 12A, 12B:
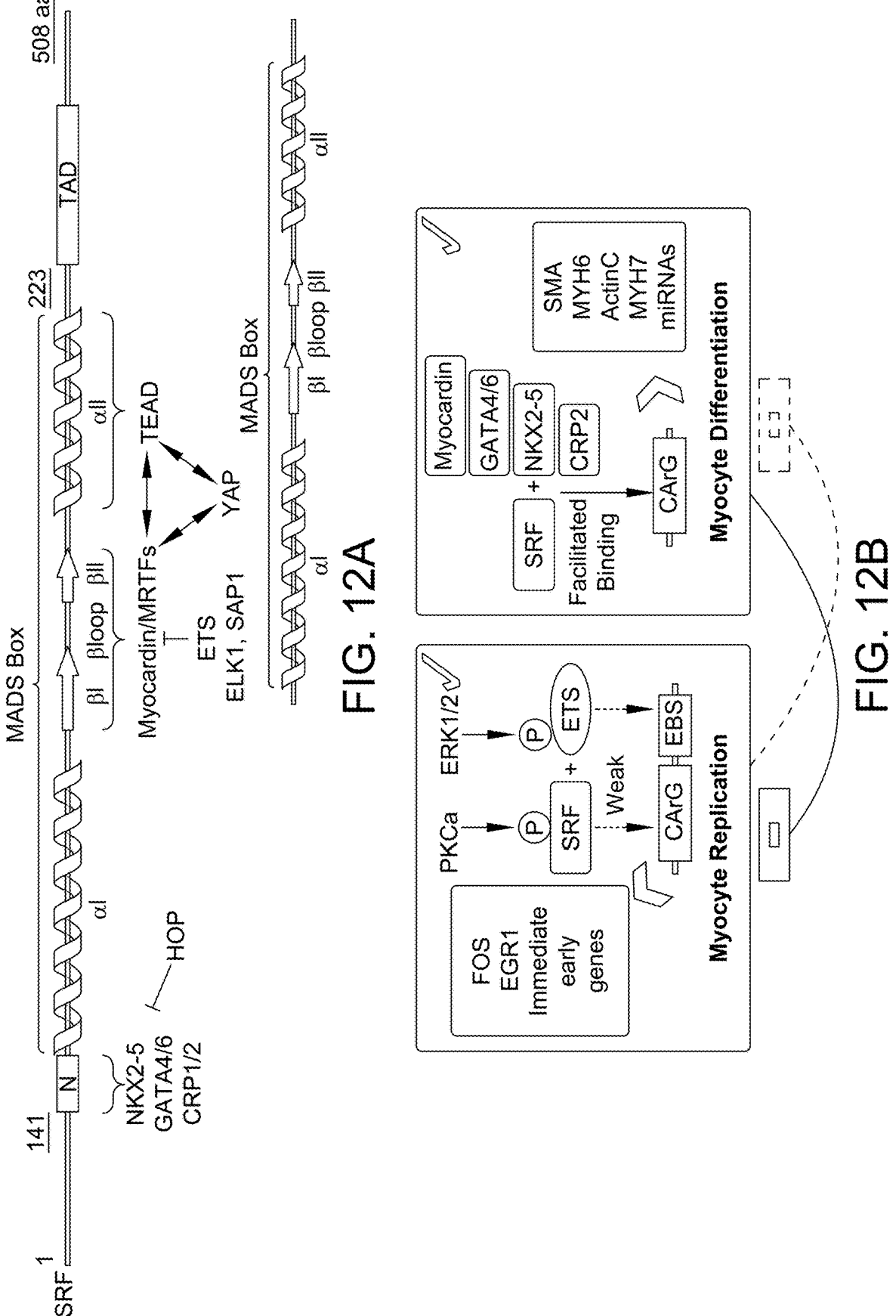
FIGS. 12A to 12F illustrate that SRF mutations block Nkx2-5 and Gata4 interaction with the MADS box inhibit DNA binding to the cardiac actin promoter and reporter 5                       6 activity.
Figures 12C, 12D, 12E, 12F:
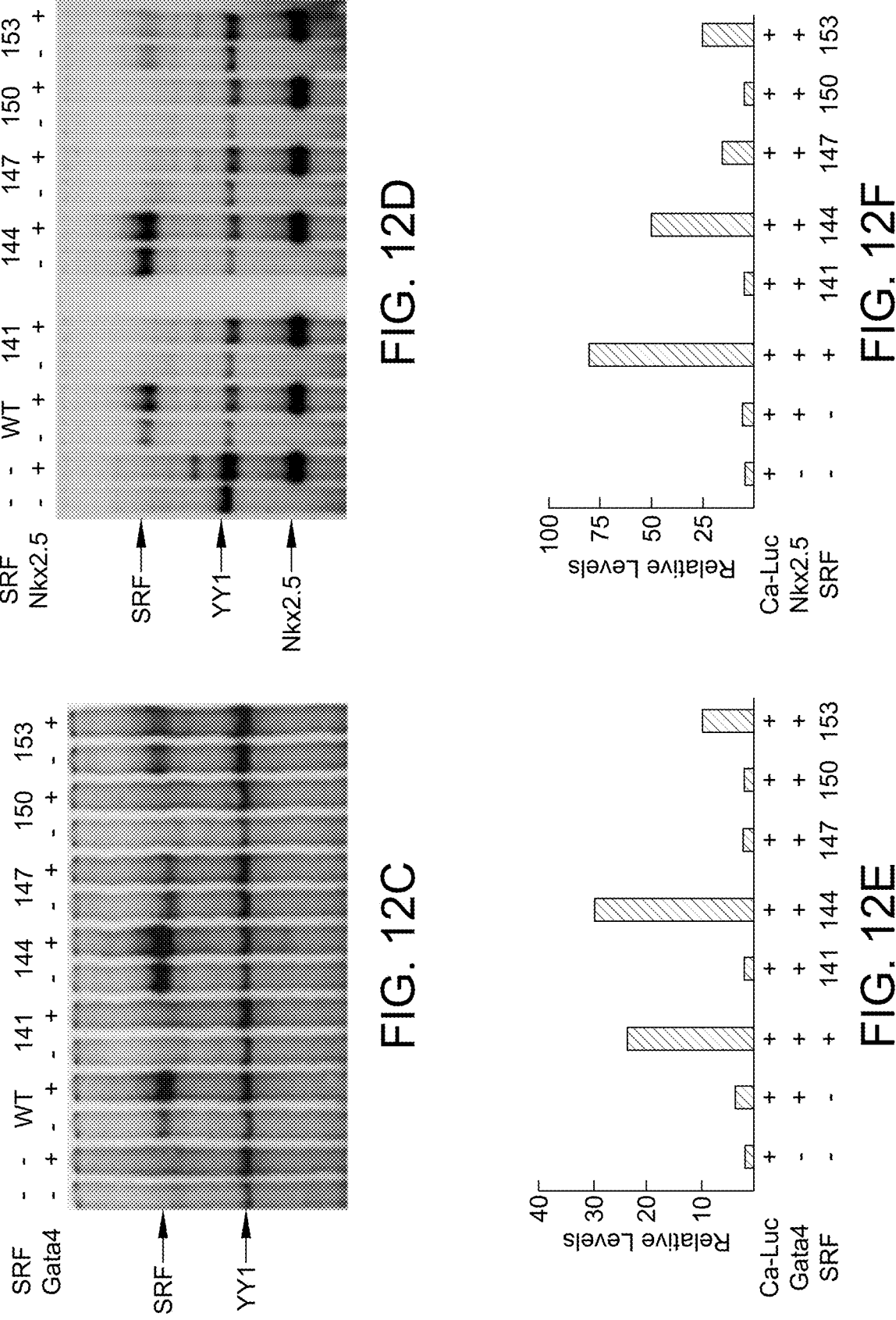

The idea that SRF activity is largely controlled by its interaction with cofactors such as Nkx2-5, Gata4, and others was tested by a "gain-of-function" approach applied to Srf-null ES cells through Lentiviral rescue of murine wild type ES cells AB2.2 and Srf$^{-/-}$ ES cells. Thus, co-factor gene expression by the lentiviral rescue of SRF null ES cells will serve, as a screening tool to evaluate co-factors' functional relationships. ES cells were maintained at the optimal conditions. Since Nkx2-5 and Gata4 facilitate SRF dependent activation of cardiac differentiated gene programs, would disrupt their co-interactions with SRF act as a default program to block differentiation and stimulate replication (FIG. 12C). FIG. 12A shows a schematic diagram of the MADS box domain binding to DNA. Triple alanine mutations were tested by electrophoretic mobility assays (EMSA) with a [P$^{32}$] labeled cardiac alpha-actin promoter DNA, in the presence of cellular lentiviral expressed Gata4 and or Nkx2-5 in comparison to control wild-type SRF. As shown by the EMSA (FIGS. 12E and 12F), Gata4, and Nkx2-5 enhanced the binding of wild-type SRF. In comparison, the triple alanine mutations starting at 141, 147, and or 150 poorly bound DNA, and their binding were not facilitated by the presence of co-expressed Nkx2-5 and Gata4; even though, Nkx2-5 showed considerable direct DNA binding to an NKX site embedded within the second and third CArG boxes. Note there are no Gata binding sites within the alpha cardiac actin promoter. The SRF153 (A3) mutant displayed weak EMSA binding that was not improved by either Gata4 and or Nkx2-5. Thus, SRF mutants that failed to shift in the EMSA assay, also failed to activate cardiac actin promoter luciferase reporter activity.

Figures 13A, 13B, 13C, 13D, 13E:
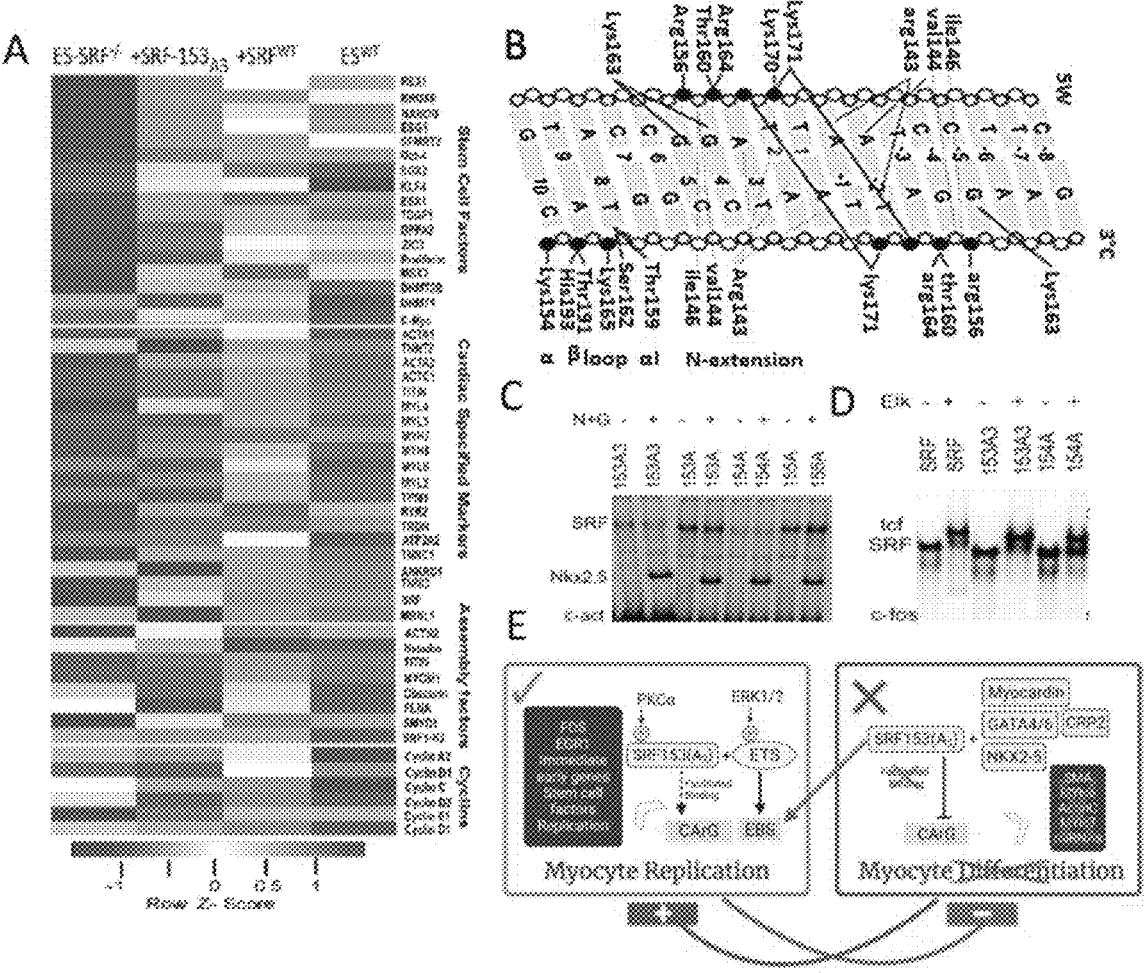
FIGS. 13A to 13E show that Stemin (153 (A3)) facilitates myocyte replication, but not myocyte differentiation in rescued SRF null murine ES cells.

Next, key triple alanine substitution mutant sites were dissected by examining single alanine amino acid mutation substitutions predicted by DNA contact sites, shown by X-ray crystal analysis (FIG. 13B) and validated by EMSA DNA binding (FIG. 13A). Single alanine substitutions at amino acid positions N153, K154, and L155 was selected. The alanine substitution at N153A and L155A did not block DNA binding but didn't facilitate SRF's EMSA with Nkx2-5 and or Gata4. FIG. 13C; 13E. The single point mutation at K154A efficiently blocked DNA binding, which could not be stabilized by Nkx2-5 and Gata4. FIG. 13C; 13E. The X-ray crystal analysis of SRF complexed with specific SRE was scrutinized and showed amino acid substitution at Lys 154 was the most critical residue for DNA binding between aa153-aa155 (FIG. 13A; 13C; 13D).

An ETS factor containing a B box, Elk1, stabilized and facilitated binding of the SRF153 (A3) and the SRF mutant K154A by binding to the c-fos promoter, which has an ETS1 binding site adjacent to the SRF binding CArG box. In contradistinction, the cardiac alpha-actin promoter does not contain ETS sites adjacent to SREs. Thus, depending on the target context the SRF mutant SRF153 (A3) will likely block cardiogenic specified genes that are dependent on Nkx2-5 and Gata4 co-association. Analysis of SRF153 (A3) binding targets by ATAC sequencing will reveal the inability of SRF153 (A3) to bind to consensus CArG sequences.

Instead, SRF153 (A3) may depend upon tethering with other transcription factors to bind to DNA targets other than CArG sequences.

The schematic diagram in FIG. 13A shows the novel activity of the Stemin, as an inhibitor of cardiac gene activity that propels cell replication. The ability for SRF to be the "myogenic driver" was completely abrogated in the SRF null ES cells. The triplet SRF mutant, SRF153 (A3) inhibited the induction of several cardiomyocyte specified genes, such as those encoding sarcomeric actins, heavy and light chain myosins, ion channels, and structural proteins. Expression of sarcomeric assembly factors such as Actinin2, Nebulin, Titin, Myomesin, Obscurin, and Smyd1 was suppressed in comparison to wild-type ES cells that formed cardiomyocytes, following hanging drop formation.

The sarcomere occupies a large volume of cardiomyocytes, which physically impedes mitosis and cytokinesis. Thus, sarcomere disassembly is a prerequisite task for cardiomyocyte proliferation. SRF153 (A3) caused sarcomere dissociation in transfected myoctes. SRF mutant SRF153 (A3), was named Stemin (SEQ ID NO: 50) because it showed powerful activation of more than 12 stem cell marker genes, such as Egr1, Rex1, Nanog, Oct4, Sox2, Zic3, Dppa2, Dnmt1, Dnmt2, and proliferin, in comparison to SRF null ES cells FIG. 13A. The expression of cyclins appeared to be repressed in the absence of SRF in the SRF null ES cells. Rescue with wild-type SRF caused activation of cyclins, CnnB1, CnnD1, CnnC, and CnnE1, while Stemin strongly induced CnnA2, CnnB1, and CnnE1. Thus, Stemin elicited an imperfect or partial pluripotency program and activated replication evidenced by the appearance of cell cycle factors. The observation that a single transcription factor, Stemin, induced the expression of stem cell factors and blocked cardiomyocyte differentiation was unprecedented.

Combination mmRNA Treated Cardiomyocytes Progress Through the Cell Cycle

Next, it was investigated whether Stemin (SEQ ID NO: 50) complements the Si knockdowns of Sal1, NF2 and Mob1 activity to drive cardiomyocyte replication. To exclude the potential low transfection rate of cardiomyocytes through plasmid DNA and the biosafety concerns of viral vectors, a modified mRNA-based transfection system was applied with optimized solutions of Stemin or YAP5SA and/or both together with Lipofectamine MessengerMAX into NRVM (neonatal rat ventricular myocytes). These young NRVM have a very low replication rate of less than 1-2% at the baseline. Stemin was added to the NRVM once at the beginning of the first day with new media changes for 6 hrs. To identify replicating myocytes, 5-ethynyl-2'-deoxyuridine (EdU) was pulsed for 8 hrs to label any myocytes synthesizing DNA during the S phase of the cell cycle. Synthetic mRNA transduced myocytes were assessed for EdU incorporation. EdU+ cell versus DAPI was counted for groups of pulse at 24-32 hrs, 32-40 hrs, and 40-48 hrs (Figure). A drop in cells centering S-phase at the last time period was observed in Stemin mmRNA and SI RNA Combination groups, indicating a transient yet efficient gene delivery. At the end of day two, counted were: the number of Troponin T (TNNT2) marked myocytes stained with anti TNNT2 (or Tnt2) that were also labeled for DNA synthesis with α-Edu and coincided with nuclear DAPI stain (FIG. 3G). Virtually all of the EdU+/DAPI stained nuclei lay within TnnT2 stained cells. Under confocal fluorescent microscopy, Stemin induced DNA replication, in 27% of the myocytes. Supporting these results, Stemin mRNA alone drives expression of pluripotent factors, Nanog and Oct4 in SRF null ES cells and 24 hours post transfected myocytes. Stemin also facilitates the expression of mitotic genes by 32 hours and DNA packaging factors, including Hist1h1a, Hist1d, Hist1h1b, Hist1h2ba and Hist3h2ba in 40 hour transfected young NRVMs.

Mob1 SiRNA synthetic mRNA, labeled 29% of the myocytes stained with EdU+/DAPI. Most exciting was the combination of Stemin and the Mob1 SI transfection of the myocytes increased co-staining of the EdU+/DAPI marked myocytes by 35% of the total number of cells. This is a likely underestimate since replicated cells may have synthesized DNA before the pulse of α-EdU. Nuclei, co-stained with α-EdU (Red) and DAPI (Blue) were observed, as pink in the merged images. Also, disorganized Tnnt2 stained myofilaments (green) were observed with labeled EdU+/DAPI nuclei. Therefore, two short pulses of Stemin and or Yap5SA induced myocyte nucleus division, in at least 27% to 35% of NRVMs.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of inducing replication of cardiac cells in a mammal, comprising:

administering to the mammal one or more of the following complementary DsiRNA pairs wherein the complementary DsiRNA pairs target the Mob1 gene and are selected from the group consisting of:

SEQ ID NOS: 43 & 44; SEQ ID NOS: 45 & 46 and SEQ ID NOS: 47 & 48.

2. The method of claim 1 wherein the mammal is a human and the complementary DsiRNA pairs are selected from the group consisting of: SEQ ID NOS: 43 & 44; SEQ ID NOS: 45 & 46 and SEQ ID NOS: 47 & 48.

3. The method of claim 1 wherein the cardiac cells are cardiomyocytes.

4. The method of claim 1, wherein the administering is by oral administration, inhalation, subcutaneous administration, intravenous administration, intraperitoneal administration, intramuscular administration, intrathecal injection, intra-articular administration, topical administration, central administration, peripheral administration, aerosol-based administration, nasal administration, transmucosal administration, transdermal administration, parenteral administration, or combinations thereof.

5. The composition of claim 1, wherein the composition comprises a delivery vehicle.

6. The composition of claim 5, wherein the delivery vehicle comprises liposomes.

\* \* \* \* \*